US007431693B2

(12) United States Patent
Pagliuca et al.

(10) Patent No.: US 7,431,693 B2
(45) Date of Patent: Oct. 7, 2008

(54) METHOD FOR ADJUSTABLY SUPPORTING AN ENDOSCOPE

(75) Inventors: James J. Pagliuca, Millis, MA (US); John D. Unger, Wrentham, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 752 days.

(21) Appl. No.: 10/985,755

(22) Filed: Nov. 10, 2004

(65) Prior Publication Data

US 2005/0085689 A1 Apr. 21, 2005

Related U.S. Application Data

(63) Continuation of application No. 09/940,402, filed on Aug. 27, 2001, now Pat. No. 6,821,243.

(51) Int. Cl.
*A61B 1/00* (2006.01)

(52) U.S. Cl. .................................. 600/102; 600/114

(58) Field of Classification Search ................. 600/101, 600/102, 114; 606/1, 130
See application file for complete search history.

(56) References Cited

U.S. PATENT DOCUMENTS

| 3,044,461 A | 7/1962 | Murdock |
| 3,822,697 A | 7/1974 | Komiya |
| 4,696,544 A | 9/1987 | Costella |
| 4,854,301 A | 8/1989 | Nakajima |
| 4,863,133 A | 9/1989 | Bonnell |
| 4,899,729 A | 2/1990 | Gill et al. |
| 5,163,949 A | 11/1992 | Bonutti |
| 5,197,971 A | 3/1993 | Bonutti |
| 5,295,994 A | 3/1994 | Bonutti |
| 5,345,927 A | 9/1994 | Bonutti |
| 5,354,302 A | 10/1994 | Ko |

(Continued)

FOREIGN PATENT DOCUMENTS

WO 02078767 10/2002

OTHER PUBLICATIONS

MEDTM presentation materials (33 pages) entitled MicroEndoscopic Discectomy System, dated 1997.

(Continued)

*Primary Examiner*—John P Leubecker
(74) *Attorney, Agent, or Firm*—Crompton, Seager & Tufte, LLC.

(57) ABSTRACT

An apparatus (100) supports an endoscope (99) for viewing a surgical site in a patient during surgery on the patient. The apparatus (100) includes a base (110), a first part (200), a second part (300), and a mechanism (400). The base (110) has a guide portion (130). The first part (200) is adapted to be fixed to the endoscope (99). The second part (300) engages the guide portion (130) and is movable relative to the guide portion (130). The second part (300) is secured to the first part (200) such that the first part (200) is movable relative to the guide portion (130). The mechanism (400) is connected between the base (110) and the second part (300). At least a portion of the mechanism (400) is rotatable to slide the first and second parts (200, 300) relative to the guide portion (130) to change a position of the endoscope (99) relative to the patient.

59 Claims, 13 Drawing Sheets

U.S. PATENT DOCUMENTS

| | | | |
|---|---|---|---|
| 5,454,365 A | 10/1995 | Bonutti | |
| 5,520,607 A | 5/1996 | Frassica et al. | |
| 5,571,072 A | 11/1996 | Kronner | |
| 5,575,754 A | 11/1996 | Konomura | |
| 5,601,590 A | 2/1997 | Bonutti et al. | |
| 5,607,386 A | 3/1997 | Flam | |
| 5,667,520 A | 9/1997 | Bonutti | |
| 5,707,359 A | 1/1998 | Bufalini | |
| 5,792,044 A | 8/1998 | Foley et al. | |
| 5,902,231 A | 5/1999 | Foley et al. | |
| 5,954,635 A | 9/1999 | Foley et al. | |
| 5,961,499 A | 10/1999 | Bonutti et al. | |
| 6,171,299 B1 | 1/2001 | Bonutti | |
| 6,187,000 B1 | 2/2001 | Davison et al. | |
| 6,338,730 B1 | 1/2002 | Bonutti et al. | |
| 6,346,072 B1 | 2/2002 | Cooper | |
| 6,358,266 B1 | 3/2002 | Bonutti | |
| 6,361,488 B1 | 3/2002 | Davison et al. | |
| 6,530,880 B2 | 3/2003 | Pagliuca | |
| 6,800,084 B2 | 10/2004 | Davison et al. | |
| 6,821,243 B2 | 11/2004 | Pagliuca et al. | |
| 2002/0010479 A1 | 1/2002 | Skakoon et al. | |
| 2002/0022764 A1 | 2/2002 | Smith et al. | |
| 2002/0087048 A1 | 7/2002 | Brock et al. | |
| 2003/0014068 A1 | 1/2003 | Bonutti et al. | |

OTHER PUBLICATIONS

Endius™ presentation materials (2 pages) entitled Spine Endoscopy System with FlexPosure, dated 1999.

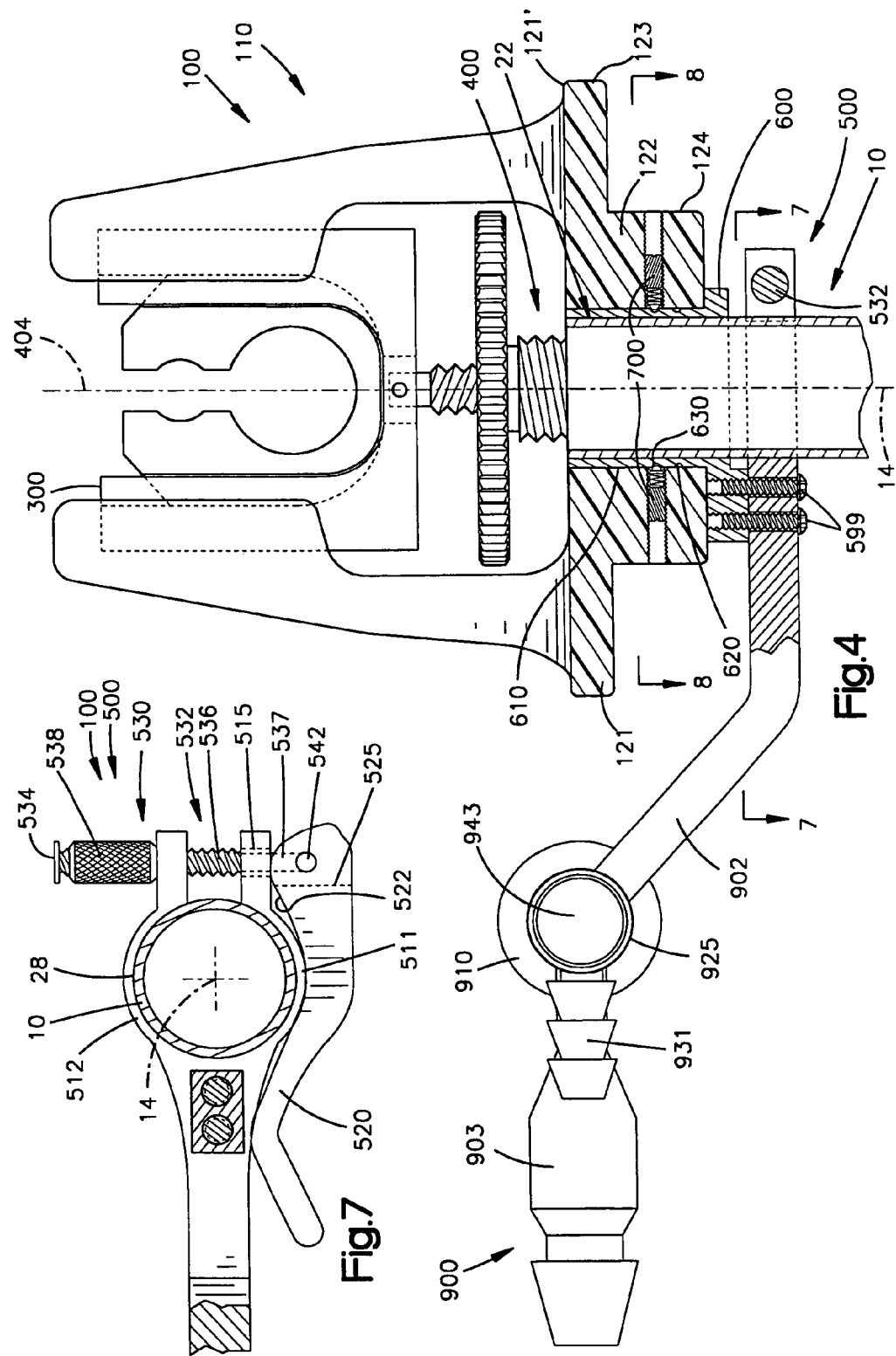

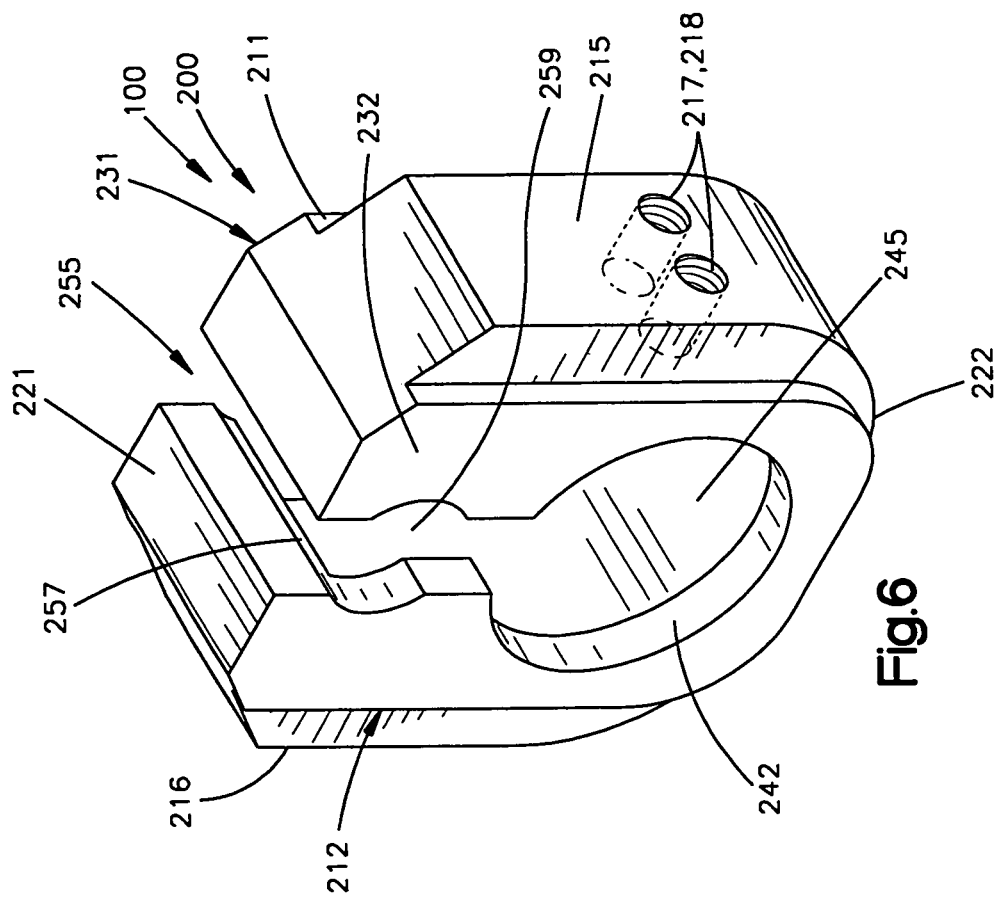
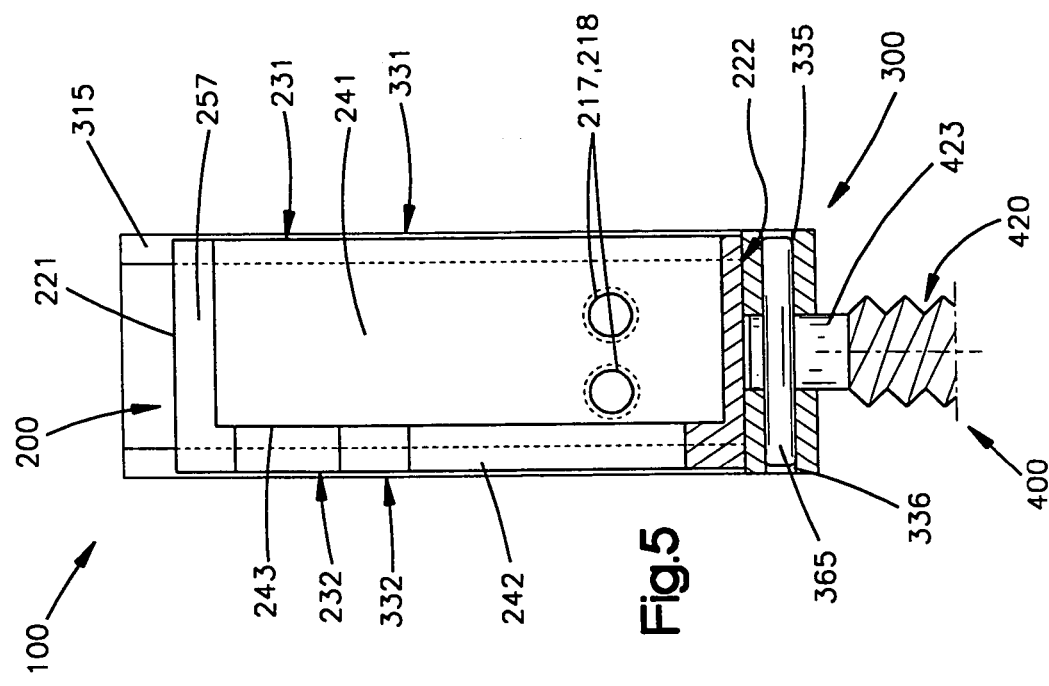
Fig.6
Fig.5

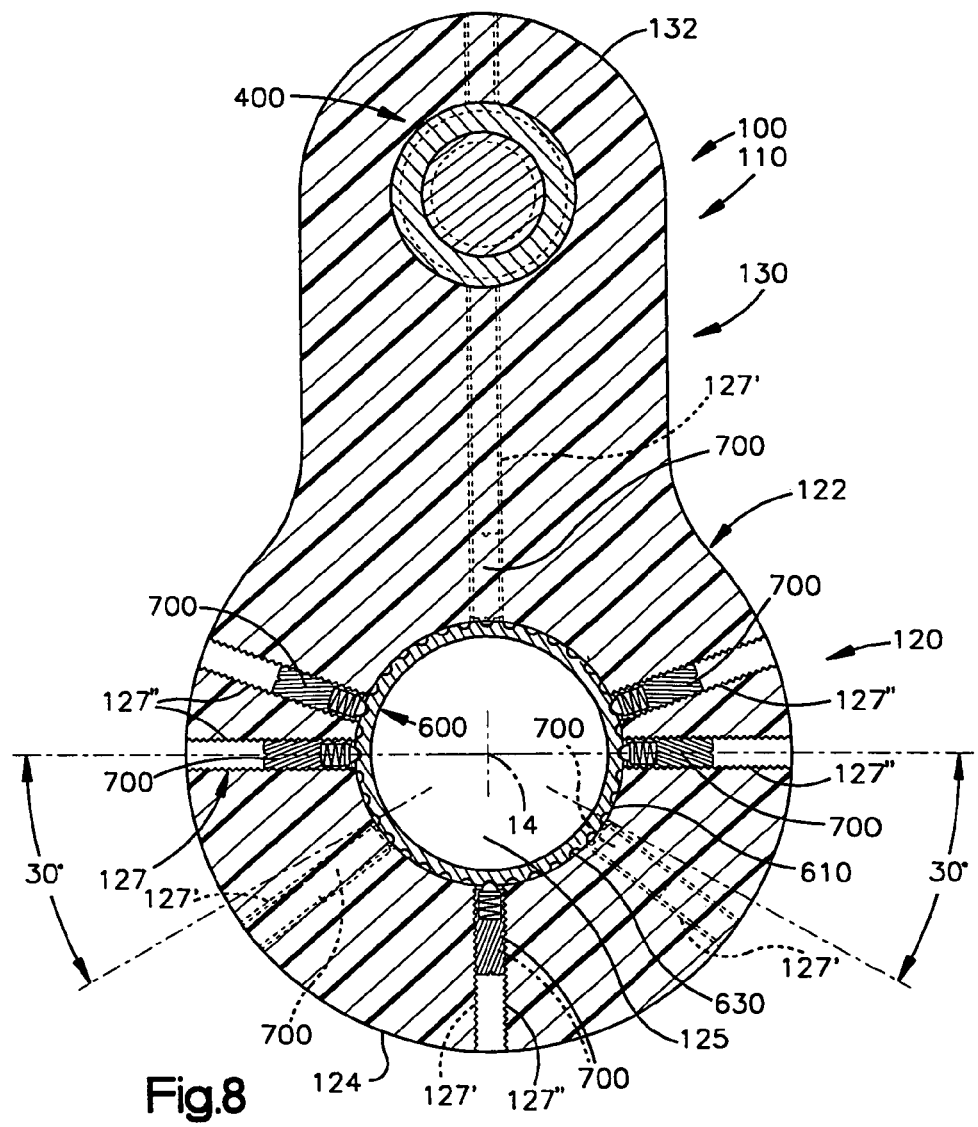
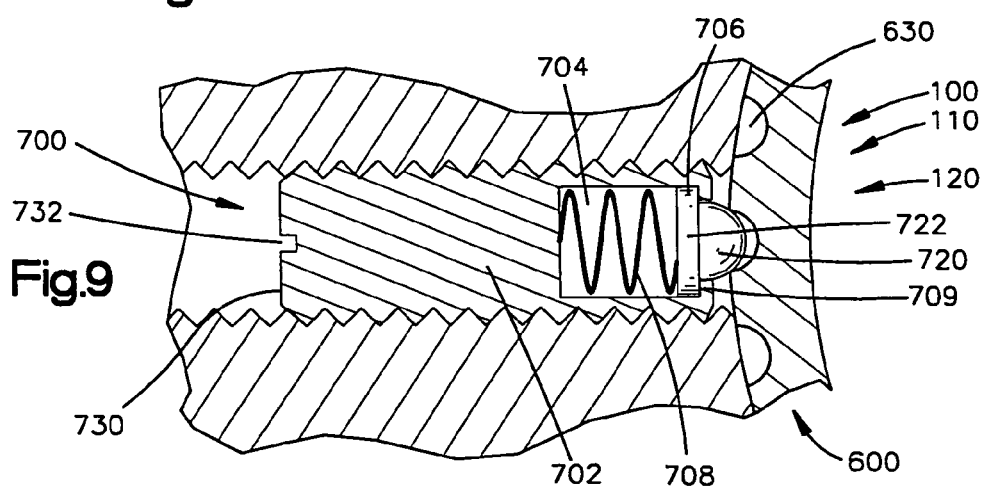

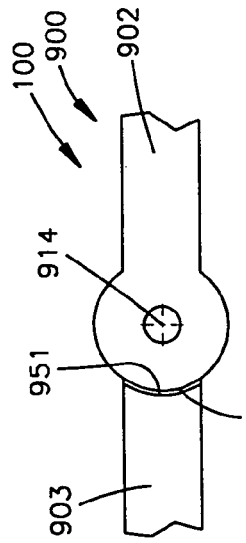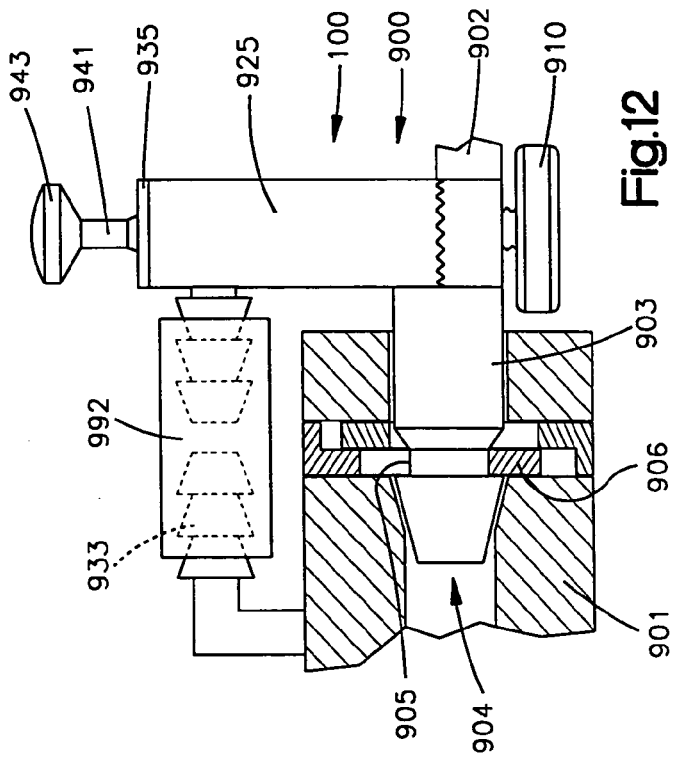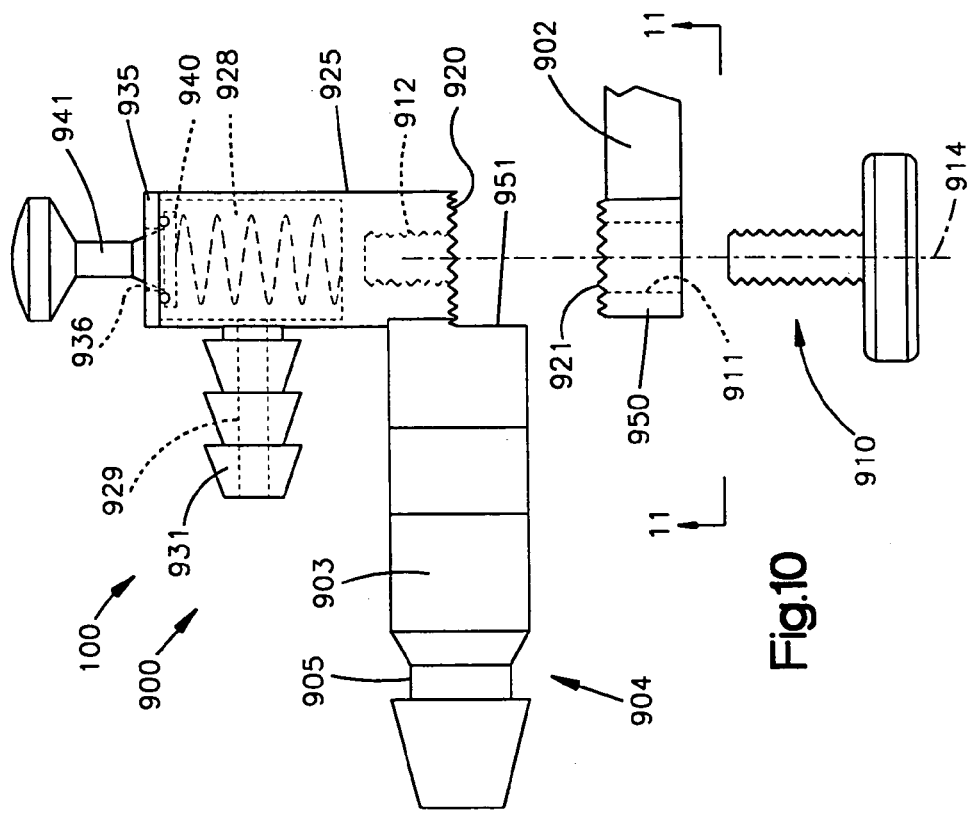

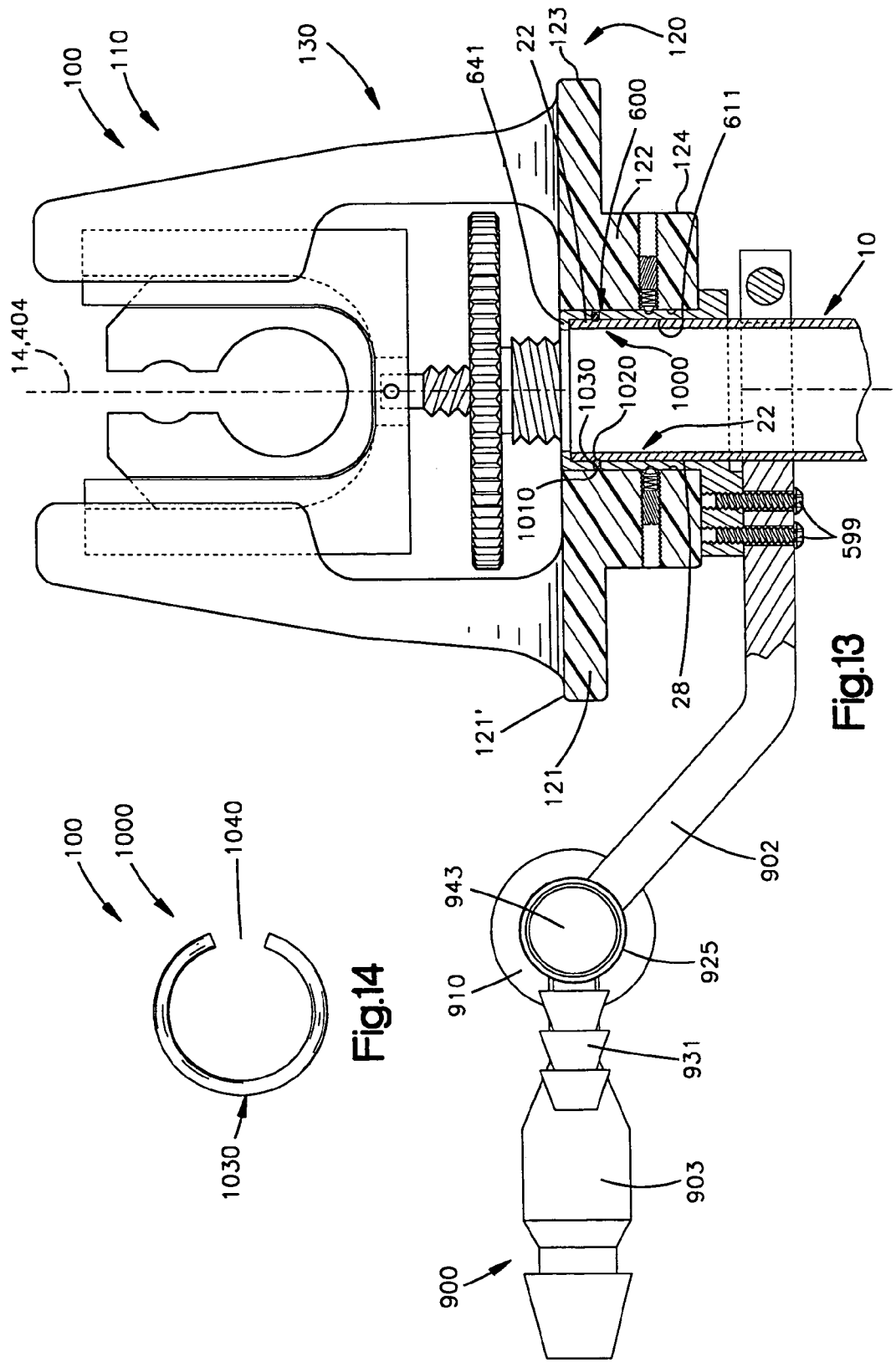

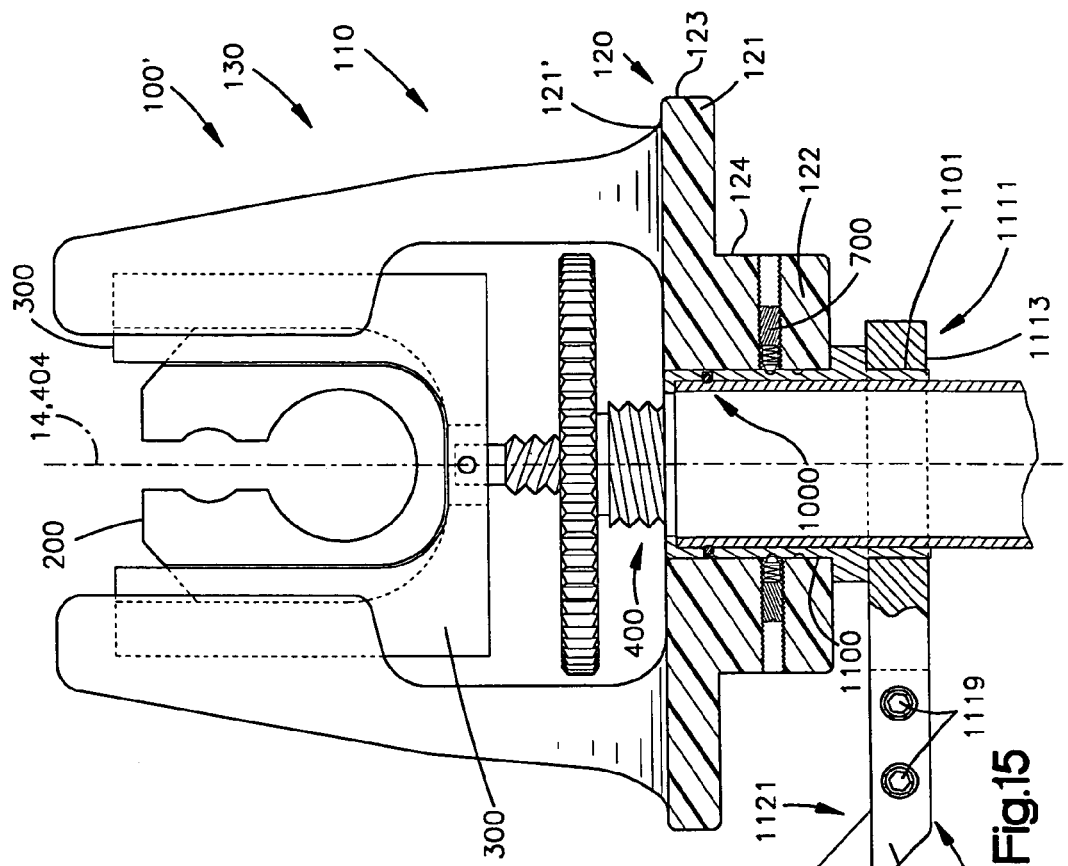
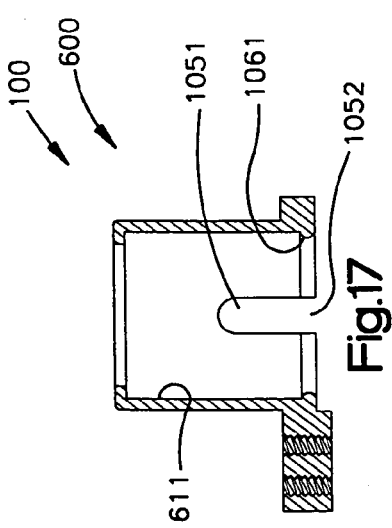
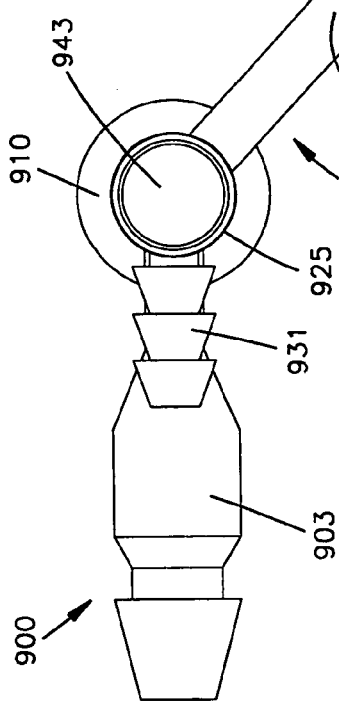
Fig. 15
Fig. 17

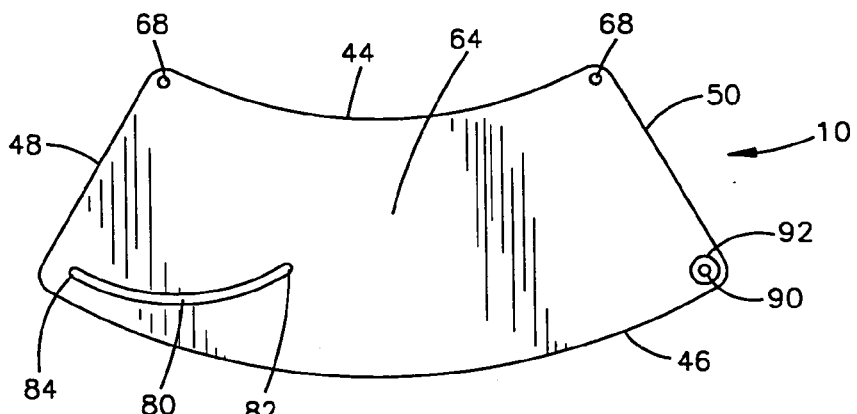
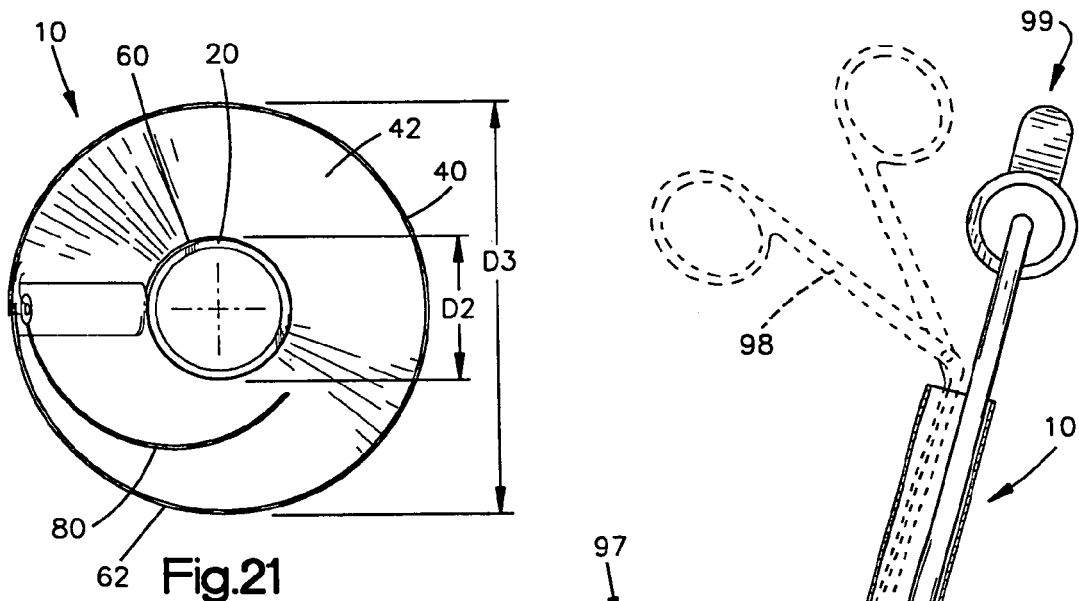
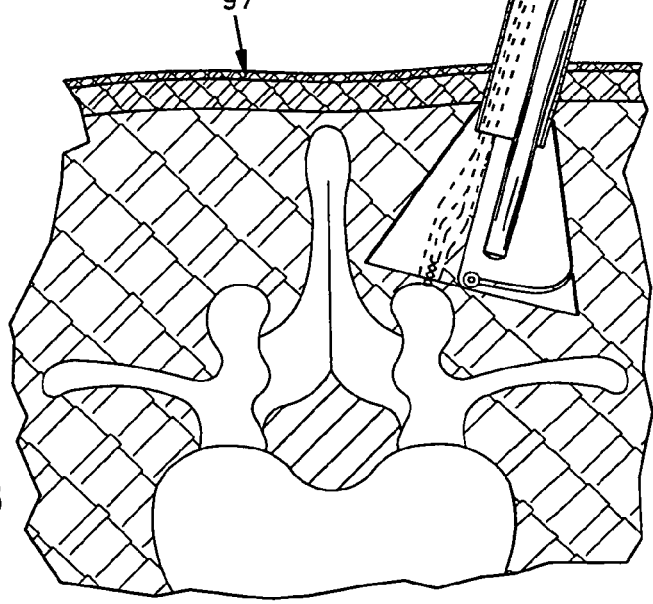
Fig.22
Fig.21
Fig.23

METHOD FOR ADJUSTABLY SUPPORTING AN ENDOSCOPE

RELATED APPLICATION

This application is a continuation of U.S. patent application Ser. No. 09/940,402, filed Aug. 27, 2001, issued as U.S. Pat. No. 6,821,243.

TECHNICAL FIELD

The present invention relates to an apparatus for adjustably supporting an endoscope and, more particularly, for supporting an endoscope for viewing different areas at a surgical site in a patient during surgery on the patient.

BACKGROUND OF THE INVENTION

Percutaneous surgery is a procedure in which surgical instruments, and typically an endoscope, are inserted through a cannula into the body of a patient. A viewing element, typically a small video camera, is part of the endoscope and is connected to a television monitor so that the surgeon may view the surgical site.

The cannula is a hollow tube. The cannula is inserted through an incision into the body of a patient. The instruments and the endoscope are inserted through the cannula. The cannula also allows the instruments and endoscope to be removed from the body and/or adjusted in the body during the surgery.

A conventional apparatus for supporting the endoscope allows a surgeon to manipulate the surgical instruments without also moving the endoscope. Also, a known support apparatus allows adjustment of the endoscope relative to the cannula for viewing different areas at the surgical site.

SUMMARY OF THE INVENTION

In accordance with one feature of the present invention, an apparatus supports an endoscope that extends through a cannula for viewing a surgical site in a patient during surgery on the patient. The apparatus includes a base, a first part, a second part, and mechanism. The base is associated with the cannula and has a guide portion. The first part is adapted to be fixed to the endoscope. The second part engages the guide portion and is movable relative to the guide portion. The first and second parts are movable together relative to the guide portion. The mechanism is connected between the base and the second part for moving the first and second parts relative to the guide portion to change a position of the endoscope relative to the patient.

In accordance with another feature of the present invention, an apparatus supports an endoscope for viewing a surgical site in a patient during surgery on the patient. The endoscope extends through a cannula into the patient. The apparatus includes a base and a cannula retainer. The cannula retainer engages an outer surface of the cannula to secure the cannula to the cannula retainer. The cannula retainer includes a split ring for engaging a groove on the outer surface of the cannula and a sleeve for receiving the cannula and supporting the split ring. The base is rotatable relative to the sleeve about an axis of the cannula.

In accordance with still another feature of the present invention, an apparatus supports an endoscope for viewing a surgical site in a patient during surgery on the patient. The endoscope extends through a cannula into the patient. The apparatus includes a base, a sleeve, and a sleeve retainer. The base supports the endoscope. The sleeve engages an outer surface of the cannula. The base and sleeve are relatively rotatable about an axis of the cannula. The sleeve retainer supports the sleeve and the base. The sleeve retainer includes a member press fit onto an end portion of the sleeve.

In accordance with yet another feature of the present invention, an apparatus supports an endoscope for viewing a surgical site in a patient during surgery on the patient. The endoscope extends into a cannula and into the patient. The apparatus includes a base, a sleeve, and a support arm. The base supports the endoscope. The sleeve engages an outer surface of the cannula. The base and sleeve are relatively rotatable about an axis of the cannula. The support arm secures the sleeve to a support structure. The support arm includes a first portion for connection to the sleeve and a second portion for interconnecting the first portion and the support structure. The first portion comprises an electrically insulating material electrically insulating the sleeve from the second portion.

In accordance with still yet another feature of the present invention, an apparatus supports an endoscope for viewing a surgical site in a patient during surgery on the patient. The apparatus includes a base, a first part to be fixed to an endoscope, a second part, a screw mechanism, and a pin. The base has a guide portion. The second part is movable in the guide portion and connected with the first part. The first and second parts are movable together relative to the guide portion. The screw mechanism is connected to the second part and is operable to move the first and second parts relative to the guide portion. The pin secures the second part to the screw mechanism. The pin is press fit into recesses in both the second part and the screw mechanism.

In accordance with yet another feature of the present invention, an apparatus supports an endoscope for viewing a surgical site in a patient during surgery on the patient. The endoscope extends through a cannula into the patient. The apparatus includes a base and a sleeve. The base supports the endoscope. The sleeve engages an outer surface of the cannula. The base and sleeve are relatively rotatable about an axis of the cannula. The sleeve has an internal diameter that increases from an initial diameter as the cannula is inserted into the sleeve and that subsequently springs back toward the initial diameter so that the sleeve grips the cannula.

In accordance with still another feature of the present invention, an apparatus supports an endoscope for viewing a surgical site in a patient during surgery on the patient. The apparatus includes a base, a structure, and a screw mechanism. The base has a guide portion. The structure is adapted to be fixed to the endoscope. The structure engages the guide portion and is movable relative to the guide portion. The screw mechanism is connected between the base and the structure. At least a portion of the screw mechanism is rotatable to slide the structure relative to the guide portion to change a position of the endoscope relative to the patient. The screw mechanism includes a first threaded spindle having female threads and a second threaded spindle rotatable about an axis relative to the female threads in the first threaded spindle. The first threaded spindle has a lip portion for limiting axial displacement of the first threaded spindle relative to the second threaded spindle.

BRIEF DESCRIPTION OF THE DRAWINGS

The foregoing and other features of the present invention will become more apparent to one skilled in the art upon consideration of the following description of the invention and the accompanying drawings, in which:

FIG. 4 is a schematic sectional view taken along line 4-4 in FIG. 2;

FIG. 5 is a schematic view partially in section of part of the apparatus of FIG. 1;

FIG. 6 is a schematic perspective view of a portion of FIG. 5;

FIG. 7 is a schematic sectional view taken along line 7-7 in FIG. 4;

FIG. 8 is a schematic sectional view taken along line 8-8 in FIG. 4;

FIG. 9 is a schematic detail view of part of the apparatus in FIG. 8;

FIG. 10 is an exploded schematic view of part of the apparatus of FIG. 1;

FIG. 11 is a schematic view taken along line 11-11 in FIG. 10;

FIG. 12 is a schematic view showing the parts of FIG. 10 with an associated mechanical arm;

FIG. 13 is a schematic sectional view similar to FIG. 4 showing features of the present invention;

FIG. 14 is a schematic detail view of part of the apparatus of FIG. 13;

FIG. 15 is a schematic sectional view similar to FIG. 4 showing features of the present invention;

FIG. 17 is a schematic detail view of a part that could be used in the apparatus of FIG. 16;

FIG. 21 is a schematic end view showing the cannula of FIG. 19 in the expanded position;

FIG. 22 is a rollout view of a part of the cannula of FIG. 19;

FIG. 23 is a schematic sectional view of the cannula of FIG. 19 during a surgical procedure.

DESCRIPTION OF A PREFERRED EMBODIMENT

Figure 20:
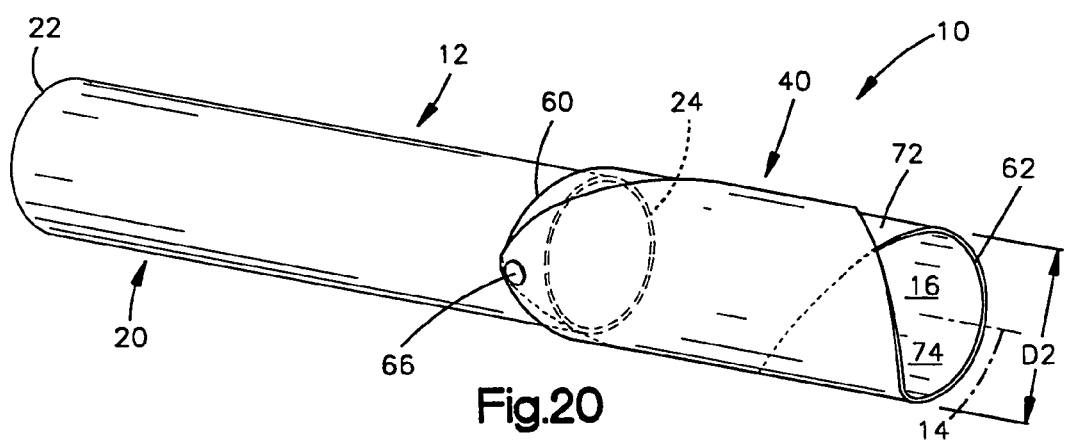
FIG. 20 is a perspective view of the cannula of FIG. 19 with parts removed for clarity, the cannula being shown in a contracted condition.

As representative of the present invention, the Figures illustrate an apparatus 100 (FIG. 1) for use in percutaneous surgery in association with a cannula 10 (FIG. 20). The apparatus 100 includes a base 110, a structure comprising a first part 200 and a second part 300, a screw-mechanism 400 connected between the base and the second part, and a cannula clamp 500 connected with the base. The first part 200 is adapted to be fixed to a camera head 99. The second part 300 is adapted to be secured to the first part. The cannula clamp 500 is adapted to be clamped to the cannula 10. The base 110, first part 200, second part 300, and camera head 99 are rotatable relative to the cannula clamp 500.

A conventional cannula is a cylindrical metal or plastic tube with a channel extending completely through the cannula. The channel has a central axis.

The cannula is inserted through an incision into a body of a patient during surgery.

FIGS. 19-23 illustrate one suitable cannula 10 constructed for use with an apparatus 100. U.S. patent application Ser. No. 09/772,605, filed Jan. 30, 2001 in the names of Thomas Davison et al., discloses other cannula structures that may be used with the apparatus 100. A specific cannula structure is not envisioned as part of the present invention. The cannula 10 will be described below by way of example of a cannula usable with the present invention.

The cannula 10 (FIGS. 19-23) is a tubular structure 12 centered on a central axis 14. The tubular structure 12 defines a passage 16 through the cannula 10. Surgical instruments and an endoscope are inserted into a patient's body through the passage 16 during surgery.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 that is preferably in the range from 10 mm to 30 mm.

The second tubular portion 40 of the tubular structure 12 is attached to the distal end 24 of the first tubular portion 20. The second tubular portion 40 is preferably made from stainless steel, but could alternatively be made from another suitable material.

As best seen in the rollout view of FIG. 22, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 19 and 20), respectively, of the second-tubular portion. The first and second ends 60, 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 22) at the first end 60 of the second tubular portion 40. The first end 60 of the second tubular portion 40 is pivotable about the rivet 66.

The second tubular portion 40 includes parallel inner and outer surfaces 70 and 72 (FIGS. 19 and 20), respectively, extending between the first and second ends 60 and 62. The inner surface 70 defines a second is passage portion 74 of the passage 16 through the cannula 10 that extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 19:
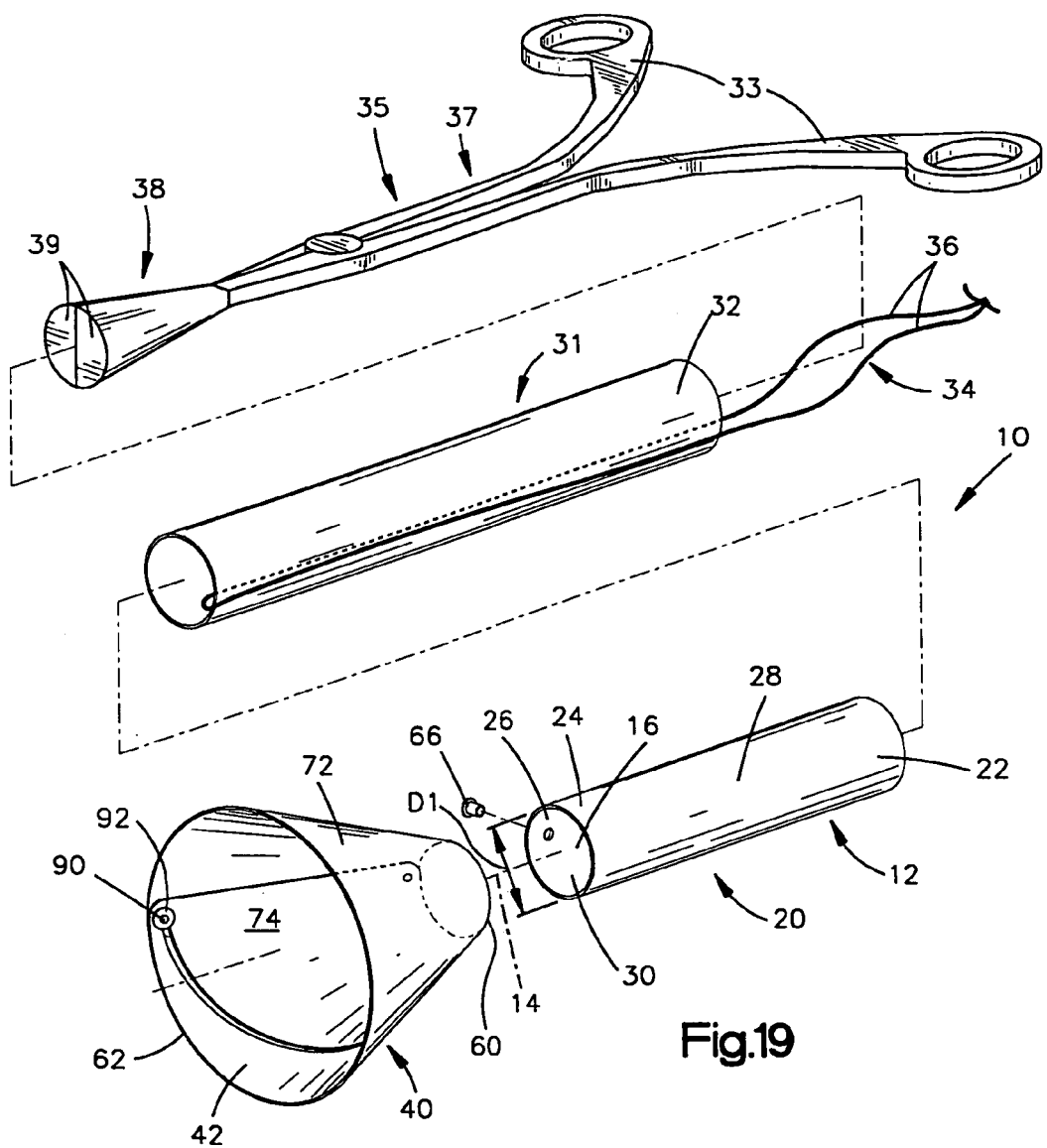
FIG. 19 is an exploded schematic view illustrating an expandable cannula constructed for use with the present invention.

The second tubular portion 40 of the tubular structure 12 is expandable from a contracted condition shown in FIG. 20 to an expanded condition shown in FIG. 19. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 20 and 21) that is approximately equal to the diameter D1 of the first tubular portion 20. Thus, the cross-sectional area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a frustoconical configuration. At the second end 62 of the second tubular portion 40, the second passage portion 74 has a diameter D3 (FIG. 21) that is larger then the diameter D2 of the second passage portion at the first end 60. Preferably, the diameter D3 of the second passage portion 74 at the second end 62 of the second tubular portion is 40% to 80% greater than the diameter D1 of the second passage portion at the first end 60.

Thus, in the expanded condition, the cross-sectional area of the second passage portion 74 at the second end 62 of the second tubular portion 40, which is a function of the diameter D3, is 16% to 64% greater than the cross-sectional area of the second passage portion at the first end 60 of the second tubular portion. In the expanded condition, the cross-sectional area of the second passage portion 74 at the second end 62 of the second tubular portion 40 may be large enough to overlie a major portion of at least two adjacent vertebrae of a patient.

The cannula 10 includes an outer layer 31 (FIG. 19) for maintaining the second tubular portion 40 of the cannula 10 in the contracted condition. It is contemplated that other suitable means for maintaining the second tubular portion 40 in the contracted condition could be employed. The outer layer 31 comprises a section of plastic tubing 32 which is heat shrunk over both the first and second tubular portions 20, 40 to hold the second tubular portion in the contracted condition.

In addition, a loop of polyester string 34 for tearing the heat shrunk tubing 32 is wrapped around the heat shrunk tubing so that it extends both underneath and on top of the tubing. An outer end 36 of the string 34 extends beyond the tubing 32.

FIG. 19 shows an actuatable device 35 for expanding the second tubular portion 40 from the contracted condition to the expanded condition. The actuatable device 35 comprises a manually operated expansion tool 37. The expansion tool 37 resembles a common pair of scissors and has a pair of legs 33 pivotally connected to one another. The expansion tool 37 includes a frustoconical end section 38 formed by a pair of frustoconical halves 39. Each of the frustoconical halves 39 extends from a respective one of the legs 33 of the expansion tool 37. It is contemplated that other suitable means for expanding the second tubular portion 40 toward the expanded condition could be employed, such as an inflatable balloon (not shown).

During an endoscopic surgical procedure, the cannula 10 is inserted into the body 97 of a patient in the contracted condition. The outer end 36 of the string 34 is then manually pulled on by the surgeon. Pulling on the string 34 tears the heat shrunk tubing 32 most of the way along the heat shrunk tubing, which frees the second tubular portion 40 for expansion. The heat shrunk tubing 32, in its torn condition, may remain attached to the first tubular portion 20.

Next, the expansion tool 37 is inserted into the passage 16 in the cannula 10 until the frustoconical end section 33 is located at the second end 62 of the second tubular portion 40. The legs 33 of the expansion tool 37 are manually separated, causing the frustoconical halves 39 to separate also. As the halves 39 separate, a radially outward directed force is exerted on the inner surface 70 of the second tubular portion 40 by the halves 39, causing the second tubular portion to expand toward the expanded condition. Under the force of the expanding expansion tool 37, the guide pin 90 slides from the first terminal end 82 of the arcuate slot 80 to the second terminal end 84 of the arcuate slot to permit the expansion of the second tubular portion 40. The expansion tool 37 can be rotated about the central axis 14 to ensure that the second tubular portion 40 of the cannula 10 is completely expanded to the expanded condition. The expansion tool 37 is then collapsed and removed so that one or more surgical instruments (indicated schematically at 98 in FIG. 23) and an endoscope (indicated schematically as part of the camera head 99 in FIG. 23) can be received through the cannula 10 and inserted into a patient's body 97 (typically at 15° from vertical as shown in FIG. 23). The expanded second tubular portion 40 of the cannula 10 provides a large working area for the surgeon inside the body 97.

The expanded tubular portion 40 can dilate and locally retract and separate spinalis muscle and soft tissues from the vertebrae thereby creating an endoscopic operating field at the surgical site. This endoscopic operating field within the spinal muscles differs from arthroscopic, laparoscopic, or cystoscopic working spaces in that there is no physiologic space or defined tissue plane that is insufflated with air or distended with fluid.

Figure 1:
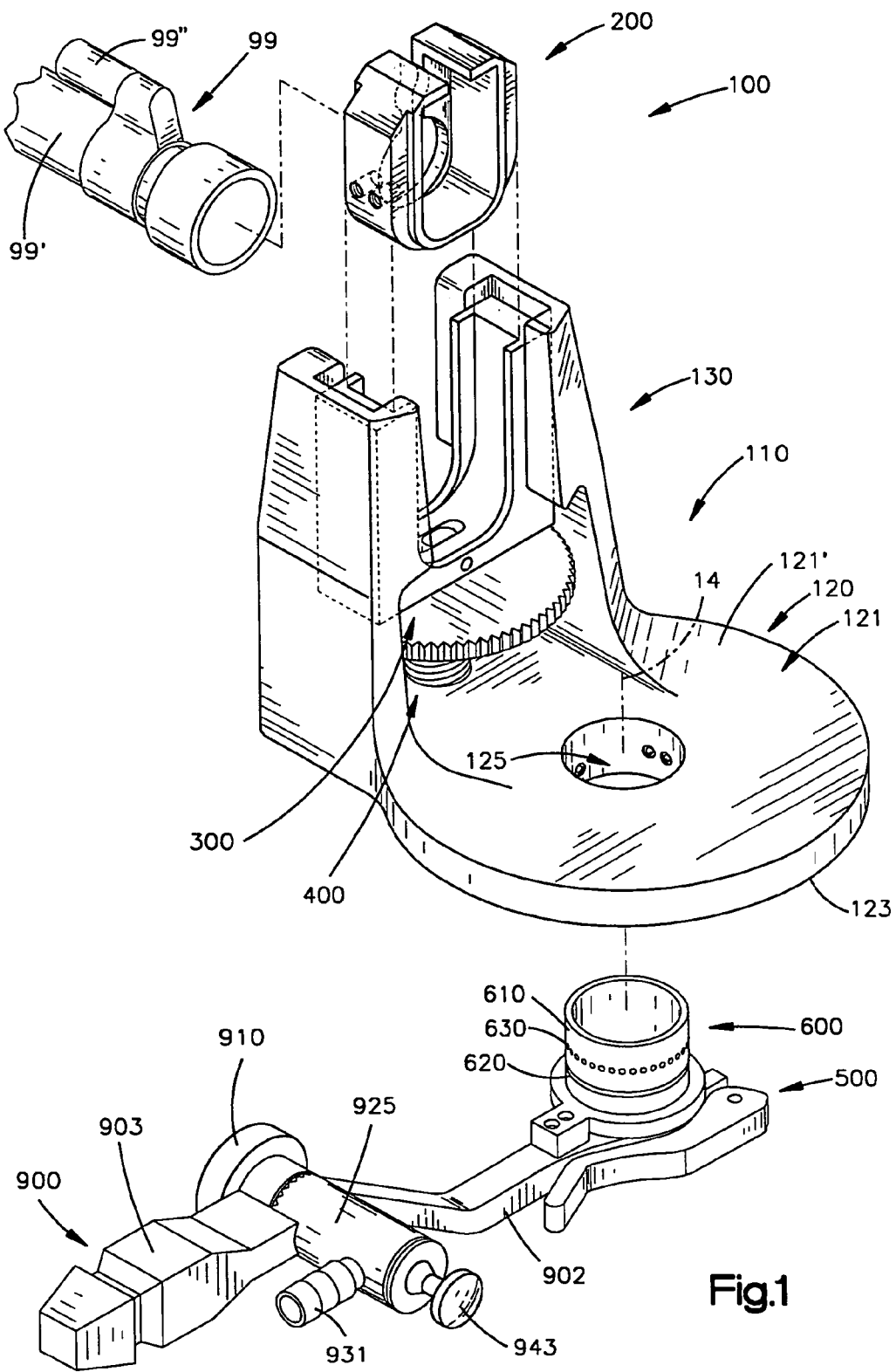
FIG. 1 is an exploded perspective view of an apparatus constructed in accordance with features of the present invention.

As viewed in FIG. 1, the apparatus 100 of the present invention may be associated with the cannula 10 of FIGS. 19-23. The base 110 of the apparatus 100 includes a base portion 120 and a guide portion 130. The base portion 120 is typically molded as one piece with the guide portion 130. The base 110 may be constructed as a suitable polymer such as polyetheretherketone (PEEK).

The base portion 120 comprises a first generally cylindrical platform, or first disk 121, and a second generally cylindrical understructure, or second disk 122 (FIG. 4). The first disk 121 has an upper circular surface area 121'. The first disk 121 has a first circular perimeter 123, and the second disk 122 has a second, smaller circular perimeter 124. A central, circular aperture 125 in the central area of the first and second disks 121, 122 extends through the disks. The first and second perimeters 123, 124 have a center 126 (FIG. 2) located at the center of the central aperture 125.

A generally cylindrical sleeve part 600 is secured to the cannula clamp 500 by conventional fasteners 599 (FIG. 4). The sleeve part 600 is located in the central aperture 125. The proximal end 22 of the cannula 10 can be easily inserted into, and removed from, the sleeve part 600. When the cannula 10 is located in the sleeve part 600, an axis of the sleeve part extends through the center 126 of the central aperture 125 and is coincident with the central axis 14 of the cannula. The axis of the sleeve part 600 also extends through the center 126 of the central aperture 125. Thus, the cannula 10 and the sleeve part 600 are concentric about the central axis 14.

Figure 3:
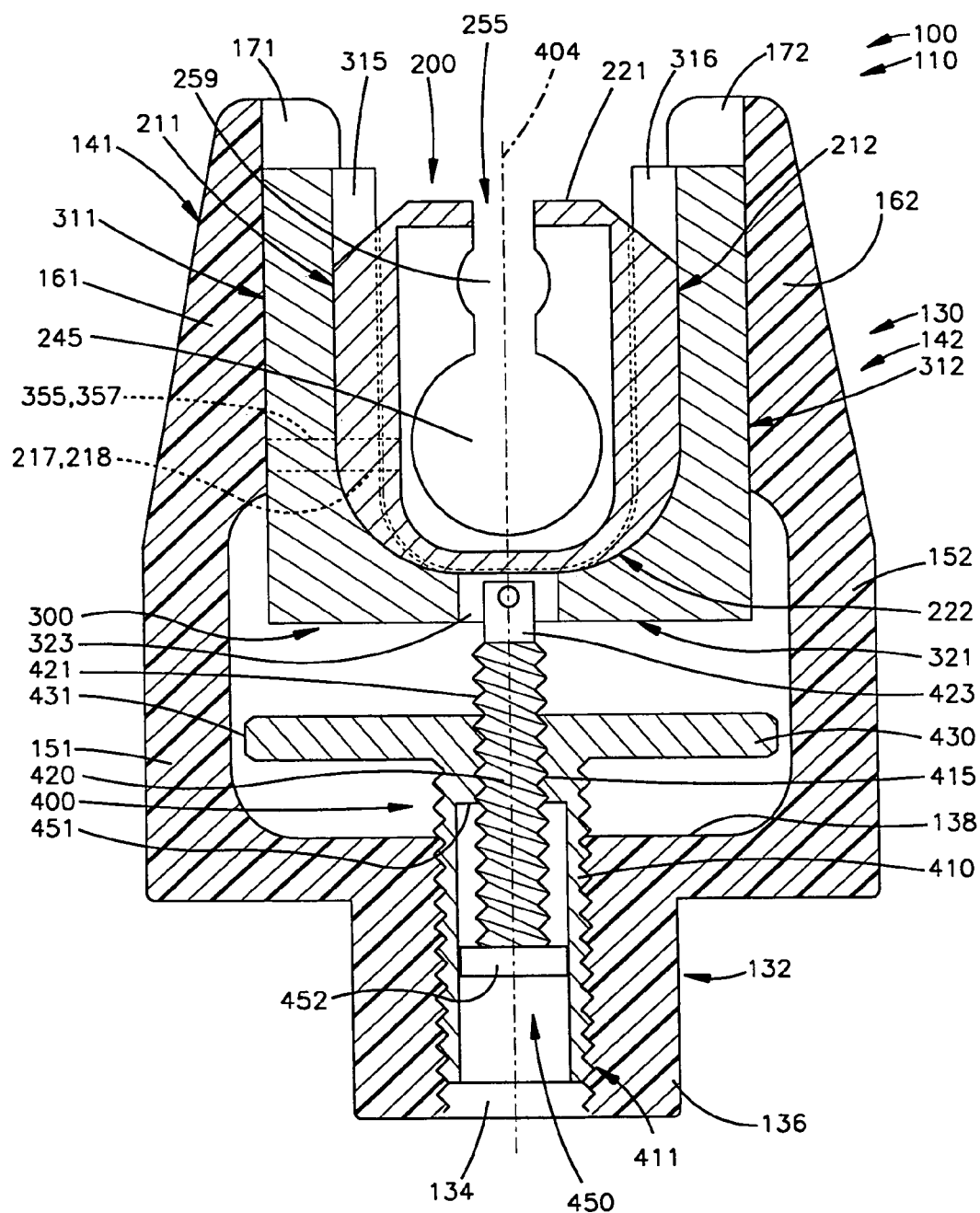
FIG. 3 is a schematic sectional view taken along line 3-3 in FIG. 2.

As viewed in FIG. 3, the guide portion 130 of the base 110 includes a horizontal base part 132, a first upright member 141 extending upward from the base part, and a second upright member 142 extending upward from the base part. The upright members 141, 142 have respective lower portions 151, 152 extending upward and parallel to each other. The upright members 141, 142 further have respective upper portions 161, 162 extending upward from the lower portions 151, 152 and toward each other. Each upper portion 161, 162 has a respective vertical, linear track 171, 172 for slidingly receiving the second part 300.

The base part 132 of the guide portion 130 has a right-hand threaded bore 134 extending vertically from a lower surface 136 of the base part to an upper surface 138 of the base part. The upper surface 138 is located between the upright members 141, 142.

Figure 2:
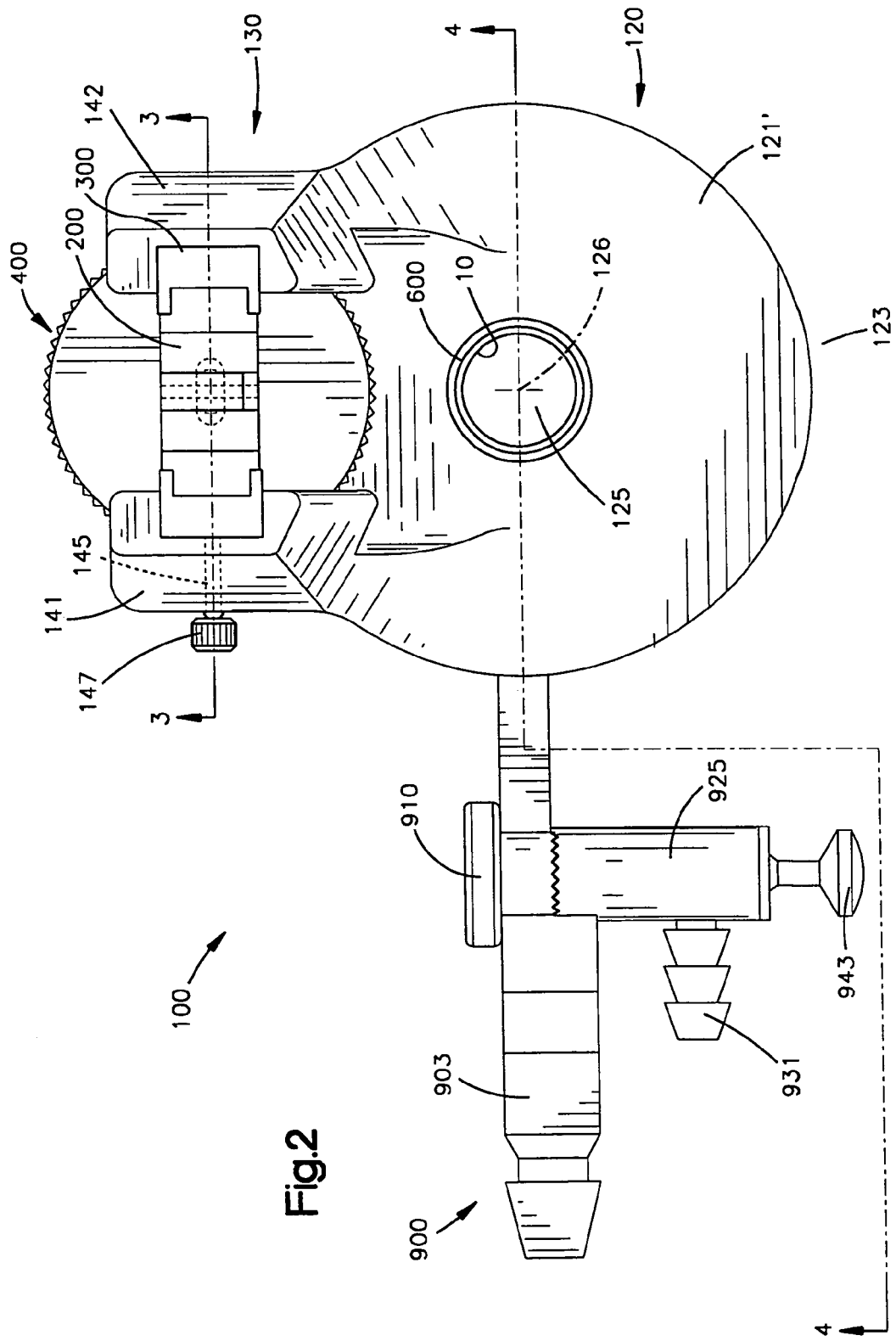
FIG. 2 is a schematic top view of the apparatus of FIG. 1.

As viewed in FIG. 2, one of the upright members 141, 142 may have a horizontal threaded bore 145 for receiving a stop member 147. The stop member 147 has a partially threaded shaft with a non-threaded end that extends horizontally through the upright member 141 or 142 into the area between the upright members 141, 142. The non-threaded end acts as a vertical limit stop for a part 430 of the screw mechanism 400.

As viewed in FIG. 1, the first part 200 connects to the camera head 99. The camera head 99 consists of a main body portion 99' and a light port 99". An endoscope (not shown) may be threaded into the main body portion 99' and secured to the main body portion. Part of the endoscope (FIG. 23) may thereby extend through the channel 12 of the cannula 10 into the patient's body 97.

The first part 200 comprises a generally U-shaped body having a passage through which the endoscope extends. As viewed in FIGS. 3 and 6, the first part 200 includes five planar surfaces and one cylindrically shaped bottom surface. These surfaces define first and second opposite, generally rectangular guide surfaces 211, 212 (FIG. 3), a generally rectangular first engagement surface 221 (FIG. 5), a second cylindrically shaped engagement surface 222 (FIG. 5), and first and second opposite, generally rectangular lateral surfaces 231, 232. The guide surfaces 211, 212 include rail members 215, 216 for slidably engaging the second part 300.

As viewed in FIG. 5, the passage in the first part 200, through which the camera head 99 extends, includes a first generally rectangular passage portion 241 and a second passage portion 242 sized for receiving and engaging the main body portion 99'. A transition point 243 in the passage is located where the first passage portion 241 and the second passage portion 242 come together.

The first passage portion 241 extends horizontally from the first lateral surface 231 through about ⅔ of the distance between the lateral surfaces 231, 232 to the transition point 243. The second passage portion 242 includes a cylindrical passage portion that communicates with the first passage portion 241 and extends horizontally from the transition point 243 to the second lateral surface 232. The second passage portion 242 forms a first circular opening 245 in the lateral surface 232. The perimeter of the first circular opening 245 forms a surface for tightly engaging the main body portion 99' of the camera head 99.

The first part 200 further includes a slot 255 for receiving the light port 99" of the camera head 99 and, an electric cord (not-shown) of the endoscope. The slot 255 extends vertically upward from the first and second passage portions 241, 242 that receive the main body portion 99'. The slot 255 intersects the first engagement surface 221. The slot 255 extends horizontally from the first lateral surface 231 to the second lateral surface 232 and intersects the lateral surfaces. The portion of the slot 255 that is adjacent the first passage portion 241 is defined by curved edges 257 for abuttingly engaging the curved outer surface of the light port 99".

The second lateral surface 232 further includes a second circular opening 259 (FIG. 6). The second circular opening 259 is sized tightly engage the curved outer surface of the light port 99". The second circular opening 259 has a smaller diameter than the first circular opening 245. The curved edges 257 of the slot 255 extend a part of the circle defined by the second circular opening 259 from the transition point 243 to the first lateral surface 231.

One of the guide surfaces 211, 212 may have one or two threaded bores 217 extending horizontally from the guide surfaces to the first passage portion 241. These bores 217 may have set screws 218, such as conventional threaded fasteners, or ball plungers 700 (discussed below), threaded into them for engaging and releasably securing the camera head 99 to the first part 200.

The second part 300 comprises a generally U-shaped body having a passage for receiving the first part 200. The second part 300 includes five planar external sides and one substantially open end. These sides define first and second opposite, generally rectangular guide surfaces 311, 312, a generally rectangular bottom engagement surface 321, and first and second opposite, planar U-shaped lateral surfaces 331, 332 (FIG. 5).

The engagement surface 321 of the second part 300 includes a generally rectangular slot 323 for receiving a part 423 (FIG. 5) of the screw mechanism 400. The slot 323 extends vertically upward from the engagement surface 321 to the passage of the second part 300.

Each lateral surface 331, 332 is intersected by a respective circular bore 335, 336 extending from each lateral surface to the slot 323. The bores 335, 336 are coaxial. A cylindrical pin 305 may be inserted into one of the bores 335, through an opening in the part 423 of the screw mechanism 400 and into the other bore 336 in order to secure the second part 300 to the part 423 of the screw mechanism 400. The outer diameter of the cylindrical pin 305 may be slightly larger than the inner diameter of the cylindrical bores 335, 336 and/or the opening in the part of the screw mechanism 400 so that a press fit engagement further secures the second part 300 to the screw mechanism 400.

The passage of the second part 300 includes two parallel guide tracks 315, 316 for slidably receiving the rail members 215, 216 of the first part 200. Once the camera head 99 is secured in the passage of the first part 200, the camera head and first part may be slid vertically downward, through the open end of the second part 300, into the passage of the second part along the guide tracks 315, 316 until the second engagement surface 222 of the first part 200 abuttingly engages the base of the passage of the second part 300. The base of the passage of the second part 300 may be curved for continuous engagement with the second engagement surface 222 of the first part 200 (FIG. 3). The camera head 99 and first part 200 are both thereby secured to the second part 300. The guide tracks 315, 316 of the second part 300 and the rail members 215, 216 of the first part 200 maintain the camera head 99 and first part 200 in a stable position relative to the second part as the second part is vertically adjusted along the guide tracks 171, 172 of the guide portion 130.

One of the guide surfaces 311, 312 of the second part 300 may have one or two threaded bores 355 extending horizontally from the guide surfaces to the first passage of the second part. These bores 355 may have set screws 357, such as conventional threaded fasteners, or ball plungers 700 (discussed below), threaded into them for engaging and fixedly securing the first part 200 to the second part 300. Corresponding bores 355 may be aligned with the bores 217 of the first part 200 so that the set screws 357 or ball plungers 700 may extend through both the first and second parts 200, 300 (FIG. 3).

As viewed in FIGS. 8 and 9, a ball plunger 700 is shown securing the base 110 to the sleeve part 600. Such a ball plunger 700 could optionally be replaced by a set screw 357. Each ball plunger 700, including those in the first part 200, the second part 300 and/or base 110, has an externally threaded tubular body 702 with a cylindrical cavity 704 located therein. The cavity 704 houses a projection 706 and a spring 708. The spring 708 may be of any suitable construction and urges each projection 706 against a lip portion 709 of the body 702. The lip portion 709 is located at one end of the cavity 704. Each ball plunger 700 has projections 706 with spherical detent members 720 and shoulder portions 722.

Each ball plunger 700 further includes a head portion 730 with a slot 732 for receiving a tool, such as a screwdriver. Each ball plunger 700 may be threadedly adjusted within a threaded bore to alter the distance that the spherical detent member 720 projects away from the associated threaded bore. This distance, along with the stiffness of each spring 708, will determine a holding force applied by the ball plunger 700.

As viewed in FIG. 3, the screw mechanism 400 provides for vertical adjustment of the second part 300 relative to the base 110 parallel to the central axis 14 of the cannula-10. The screw mechanism 400 includes a first large diameter spindle 410, a second small diameter spindle 420, and a thumb wheel 430. The thumb wheel 430 and the first spindle 410 rotate about a secondary axis 404 parallel to the central axis 14 and spaced apart from the central axis. The first spindle 410 and the thumb wheel 430 may be made of plastic and integrally molded together as one piece. The right-hand threaded bore 134 of the base part 132, the first spindle 410, the second spindle 420, and the thumb wheel 430 are all symmetric about the secondary axis 404.

The first spindle 410 has right-hand male threads 411 for engaging the female threads of the right-hand threaded bore 134 of the base part 132. As the first spindle 410 is rotated, due to manual force applied to the thumb wheel 430, about the secondary axis 404, the first spindle 410 moves axially along the secondary axis vertically into, or out of, the right-hand threaded bore 134 depending upon the direction of rotation. The second spindle 420 has opposite left hand male threads 421 for engaging female threads of a left-hand threaded bore 415 centered on the secondary axis 404 and located within the first spindle 410.

The upper end of the second spindle 420 has the part 423 that is a rectangular, planar end portion inserted into the slot 323 of the second part 300. Instead of the cylindrical pin 305, set screws 357 or preferably ball plungers 700 threaded into the bores 335, 336 in the second part 300, may alternatively engage planar surfaces of the end portion 423 and secure (along with the tracks 171, 172 of the base 110) the second part 300 against rotational movement relative to the second spindle 420. The cylindrical pin 305, set screws 357, or ball plungers 700 releasably secure the second part 300 against axial movement relative to the end portion 423 of the second spindle 420.

If set screws 357 or ball plungers 700 are used, the end portion 423 of the second spindle 420 may alternatively have hemispherical recesses (not shown) for receiving the end of the set screws or the spherical detent members 720 of the ball plungers. The second spindle 420 may be removed from the slot 323 of the second part 300 by removing the cylindrical pin 305, by disengaging the ends of the set screws 357 from the hemispherical recesses, or by overcoming the bias of the spherical detent members 720 in the hemispherical recesses.

As viewed in FIG. 3, the stop member 147 may alternatively be replaced by a stop structure, or limit structure 450, located internal to the first spindle 410. The limit structure includes a generally cylindrical shoulder portion 452 extending radially outward from the lower end of the second spindle 420 and a lip portion 451 extending radially inward from the upper end of the first spindle 410. As the second spindle 420 is threaded upward relative to the first spindle 410, it will reach a position where the shoulder portion 452 will abuttingly engage the lip portion 451 of the first spindle and thereby prevent the second spindle from becoming disengaged from the first spindle. The second spindle 420 can not be raised past this position relative to the first spindle 410.

The thumb wheel 430 has a knurled perimeter 431 to facilitate manual rotation of the thumb wheel about the secondary axis 404. When rotation is imparted to the thumb wheel 430, the threaded engagement between the right-hand female threads of the right-hand threaded bore 134 of the base 130 and the right-hand male threads 411 of the first spindle 410 either raises or lowers the first spindle vertically relative to the base 110 depending upon the direction of rotation. Simultaneously, the threaded engagement between the left-hand female threads of the left-hand threaded bore 415 of the first spindle 410 and the left-hand male threads 421 of the second spindle 420 either raises or lowers (depending on the direction of rotation) the second spindle vertically relative to the first spindle. This opposite hand thread arrangement results in an amplified movement of the second spindle 420 for each single rotation of the thumb %-wheel 430 because the two sets of threads work in concert to axially move the first spindle 410 and second spindle in the same direction, instead of acting against each other as would occur if the threads were both left-hand or both right-hand.

The second part 300, being secured to the end portion 423 of the second spindle 420, is moved linearly parallel to the axis 14 of the cannula 10 (or vertically) upon rotation of the thumb wheel 430. The second part 300 slides along the linear tracks 171, 172 of the guide portion 130 with the stop member 147 or limit structure 450 providing an upper limit for the position of the second part 300. As the second part 300 moves, the tracks 171, 172 may engage the lateral surfaces 331, 332 of the second part 300 and block rotation of the second part about the secondary axis 404. Further, the tracks 171, 172 guide the vertical movement of the second part 300. Upon vertical movement of the second part 300 relative to the base 110, the camera head 99 (and first part 200) are thereby vertically adjusted, since they are secured in the passage in the second part 300, as described above.

As viewed in FIG. 7, the cannula clamp 500 includes two gripper arms 511, 512 that are deflected toward each other to clamp against the outer surface 28 of the cannula 10, a gripper actuating lever 520 for deflecting the gripper arms into gripping engagement with the outer surface of the cannula, and an adjustment mechanism 530 for changing the relative position of the gripper arms from which the arms are moved by the actuating lever to enable the arms to clamp different diameter cannulas. The gripper actuating lever 520 also releases the gripper arms 511, 512 from gripping engagement with the outer surface 28 of the cannula 10. When released, the gripper arms 511, 512 will spring away from the outer surface 28 of the cannula 10. The two gripper arms 511, 512 may grip the plastic tubing 32 depending on the position of the plastic tubing on the first tubular portion 20 of the cannula 10 (as described above). References in this application to gripping the outer surface 28 of the cannula 10 are meant to also cover the gripper arms 511, 512 engaging the plastic tubing 32.

The adjustment mechanism 530 includes a threaded stud 532 with a longitudinal axis, an adjustment knob 538 with a female threaded bore, and a lock pin 542. The threaded stud 532 has a head 534, a threaded shaft 536 for screwing into, and through, the threaded bore of the adjustment knob, and an oblong, or flat end 537 which extends through an oblong bore 515 in the gripper arm 511. Alternative structures for the adjustment mechanism 530 are envisioned by the present invention.

During assembly, the flat end 537 of the threaded stud 532 is threaded through the bore of the adjustment knob 538 and inserted horizontally through a circular bore (not shown) in the gripper arm 512 that is larger in diameter than the diameter of the threaded stud and through the oblong bore 515 in the gripper arm 511. The flat end 537 of the threaded stud 532 is then horizontally (as viewed in FIGS. 4 and 7) inserted into a longitudinal slot 525 in the lever 520. The threaded stud 532 is secured against rotation relative to gripper arms 511, 512 by engaging surfaces of the gripper arm defining the oblong bore 515 on gripper arm 511. The lock pin 542 is then inserted vertically through a bore (not shown) in the lever 520 and through a bore (not shown) in the flat end 537 of the threaded stud 532 thereby securing the adjustment mechanism 530 together. The lever 520 is free to rotate about the lock pin 542.

The adjustment knob 538 may be axially positioned along the threaded stud 532 by rotation of the adjustment knob about the secured threaded stud. By changing the axial position of the adjustment knob 538, the gripper arm 512 moves relative to the threaded stud 532 and the distance between the gripper arms 511, 512 changes and the relative positions of the gripper arms change. Rotation of the adjustment knob 538 in one direction may move the gripper arms 511, 512 closer together and rotation in the opposite direction may allow the arms to spring apart.

A camming surface 522 on the lever 520, adjacent the gripper arm 511, moves the arms 511, 512 a predetermined distance together to grip the outer surface 28 of the cannula 10 as the lever is rotated clockwise about the lock pin 542 to the position shown in FIG. 12. Counterclockwise rotation of the lever 520 about the lock pin 542, from the position shown in FIG. 12, allows the gripper arms 511, 512 to spring (move) apart and releases the outer surface 28 of the cannula 10 from the cannula clamp 500.

The gripper arms 511, 512 have a normal position from which the gripper arms may be moved a predetermined distance by the actuating lever 520 to grip a cannula having a first diameter. Rotation of the adjustment knob 538 in one direction relative to the stud 532 causes arms 511, 512 to resiliently deflect toward each other and take new positions. The gripper arms 511, 512 may be moved from these new positions a predetermined distance by the actuating lever 520 to grip a cannula having a second diameter smaller than the first diameter. Rotation of the adjustment knob 538 in a second direction opposite the first direction allows the gripper arms 511, 512 to spring back toward their normal positions. The adjustment knob 538 enables the cannula clamp 500 to securely grip cannulas of different diameters.

When the cannula clamp 500 is released from the cannula 10, the base 110 and parts (i.e., the camera head 99, the endoscope, etc.) attached to the base may move axially along the central axis 14 of the cannula 10 relative to the cannula. After the apparatus 100 is initially aligned with the cannula 10, the camera head 99 may be positioned on the apparatus 100 and axially adjusted along the central axis 14 in this manner. When the cannula clamp 500 is gripping the outer surface 28 of the cannula 10, the screw mechanism 400 provides for vertical (axial) adjustment of the camera head 99 relative to the cannula.

As viewed in FIG. 1, the cylindrical sleeve part 600, which is secured to the cannula clamp 500, may be inserted into the central aperture 125 of the base 110. The sleeve part 600 has a passage extending through the sleeve part, which passage receives the cannula 10. As viewed in FIG. 4, the upper edges of the sleeve part 600 and the proximal end 22 of the cannula 10 are typically assembled flush with the upper surface area 121' of the first disk 121. The sleeve part 600 is centered about the central axis 14 and includes a cylindrical outer surface 610, a horizontal groove 620 that extends around the cylindrical outer surface, and a horizontal array of spaced apart recesses 630 in the cylindrical outer surface. The recesses 630 lie in a horizontal plane parallel to, and axially offset from, a plane defined by the groove 620, both planes being perpendicular to the central axis 14.

As viewed in FIG. 8, the sleeve part 600 is axially secured in the central aperture 125 of the base 110 by set screws 357 or, more preferably, by ball plungers 700 extending radially into the central aperture and engaging the groove 620. The sleeve part 600 is rotationally (and axially) secured in the central aperture 125 of the base 110 by the set screws 357 or the ball plungers 700 extending radially into the central aperture and being received in the recesses 630. The set screws 357 or ball plungers 700 are threaded radially inward through threaded radial bores 127 that penetrate radially inward from the second perimeter 124 of the base 110 to the central aperture 125. Three radial bores 127' are axially aligned with the groove 620 and are located at 120° increments about the central aperture 125. Five additional radial bores 127" are axially aligned with the recesses 630, three at 120° increments about the central aperture 125, but angularly offset 60° from the three bores 127' and two at diametrically opposed locations and offset 30° from two of the three bores 127".

If set screws 357 are used, the distal ends of the set screws form detents that engage the groove 620 and support the sleeve part 600 in the central aperture 125, but allow the base 110 and sleeve part to rotate relatively to the base about the central axis 14. The recesses 630 of the sleeve part 600 and the detents formed by set screws 357 form an indexing mechanism that secures the sleeve part at selected angular increments about the central axis 14 relative to the base 110. Thirty-six (36) recesses 630 are spaced about the cylindrical outer surface 610 at 10° increments. Thus, when the set screws 357 are threadedly disengaged from the recesses 630, the base 110 may be rotated about the central axis 14 relative to the cannula clamp 500 and the cannula secured thereto, while the base 110 is axially secured by the set screws 357 engaging the groove 620. After 10° of rotation (or some multiple of 10°), the set screws 357 may be threaded inward for reengaging the recesses 630 and rotationally securing the base 110 to the cannula clamp 500 and the cannula 10. An access bore 128 is located in the base part 132 of the guide portion 130 for providing access to the bore 127' that is disposed within the guide portion 130 of the base 110.

If ball plungers 700 are used, which is preferable, the spherical detent members 720 form detents that engage the groove 630 and support the sleeve part 600 in the central aperture 125, but allow the base 110 and the sleeve part to rotate about the central axis 14. The recesses 630 of the sleeve part 600 and the detents formed by ball plungers 700 form an indexing mechanism that secures the sleeve part at selected angular increments about the central axis 14 relative to the base 110. Thirty-six (36) recesses 630 are spaced about the cylindrical outer surface 610 at 10° increments. Thus, with minimal manual force to overcome the biasing force of the ball plungers 700, the base 110 may be rotated about the central axis 14 relative to the cannula clamp 500 and the cannula 10 secured thereto, thereby disengaging the biased spherical detent members 720 from the recesses 630. The base 110 will remain axially secured by the ball plungers 700 engaging the groove 620. The spherical detent members 720 reengage the recesses after 10° of rotation. The ball plungers 700 may be further secured in the bores 127 of the base 110 by adhesive being applied to the externally threaded tubular bodies 702 near each head portion 730.

However, if rotation of the base 110 more than 10° is desired, the manual force applied to the base can continue to rotate the base relative to the cannula clamp 500 and the cannula 10. As should be apparent, the base 110 and the camera head 99 (and the attached endoscope) may rotate at least 300° about the central axis 14 of the cannula 10 and be adjustably fixed at 10° increments. This enables the surgeon to view different parts of the surgical site, as desired. The sleeve part 600 of the cannula clamp 500 can be easily removed from the central aperture 125 for cleaning, maintenance, etc. of the parts by disengaging the set screws 357 from the groove 620, and the recesses 630, or by overcoming the biasing force applied by the ball plungers 700 to the sleeve part.

As viewed in FIGS. 10-12, the cannula clamp 500 is a part of the support arm 900 for attaching the apparatus 100 to a mechanical robotic arm 901. The support arm 900 includes an arm portion 902 which may be formed integrally with the gripper arms 511, 512. As viewed in FIG. 4, the arm portion 901 extends upwardly away from the gripper arms 511, 512 in order to minimize the possibility of contact with the patient during surgery.

The support arm 900 also includes an arm portion 903. The arm portion 903 has an attaching structure 904, including a groove 905, which snaps into a socket in the mechanical arm 901. Detents of any suitable type and designated 906 in the mechanical arm 901, hold the arm portion 903 in position in the socket in the mechanical arm 901. The detents 906 may be controlled by external actuation levers (not shown) on the mechanical arm 901 for manually releasing the arm portion 903 from the mechanical arm 901.

The arm portions 902, 903 are pivotally connected to each other by a fastener 910. The fastener 910 extends through an opening 911 in the arm portion 902 and threads into a threaded opening 912 in the arm portion 903. When the fastener 910 is released, the arm portions 902, 903 may pivot relative each other about a pivot axis 914. The pivot axis 914 is centered on the axis of the fastener 910 and the axis of the threaded opening 912. When the fastener 910 is tightly screwed into the threaded opening 912, the arm portions 902, 903 are secured together against pivoting movement. When the fastener 910 is released, the arm portions 903, 902 may pivot relative to each other about the axis 914.

The end of the arm portion 902, which is adjacent to the arm portion 903, has a convex surface 950, which is curved about the axis 914. The arm portion 903 has a concave surface 951, which is also curved about the axis 914. The surfaces 950, 951 move concentrically relative to each other when the arm portions 902, 903 pivot relatively about the axis 914.

The arm portion 903 has a set of teeth 920 which encircle the axis 914 and which project axially toward a set of teeth 921 on the arm portion 902. The teeth 921 project axially toward the teeth 920. The teeth 920 and the teeth 921 mesh with each other and provide a locking action so that the arm portions 902, 903 are positively locked against relative movement about the axis 914 when the fastener 910 is tightly screwed into the opening 912. The teeth 920, 921 define a lock which blocks relative rotation of the arm portions 902, 903 about the axis 914. When the fastener 910 is loosened, the arm portions 902, 903 may be rotated relative to each other about the axis 914, and thus, the arm portions 902, 903 may pivot relative to each other to adjust the position of the apparatus 100.

A cylindrical projection 925 is welded to the arm portion 903. Thus, the projection 925 and arm portion 903 are fixedly connected together. The projection 925 is centered on the axis 914 and contains a chamber 928.

As viewed in FIG. 12, the chamber 928 communicates with a fluid passage 929 in a male fluid connector 931. The male connector 931 attaches to a male connector 933 on the mechanical arm 901 by means of a flexible hose 992 so that the fluid passage 929 communicates with a fluid passage in the mechanical arm 901.

As viewed in FIG. 10, the chamber 928 is closed at its upper end by a cap 935. The cap 935 has an opening 936 centered on the axis 914. The opening 936 communicates with the chamber 928. A manually movable internal valve member 940 normally closes the opening and blocks the chamber 928 from communicating with the ambient air surrounding the support arm 900. The valve member 940 is connected to a stem 941, which is also centered on the axis 914. The stem 941 has a knob or button 943 on its end that may be manually depressed to move the stem 941 and valve member 940 downward (as viewed in FIG. 10) into the chamber 928. When the stem 941 and valve member 940 are so moved, the chamber 928 is in communication with the ambient air surrounding the device due to the unblocking of the opening 936.

The mechanical arm 901 is a known device and is of the type generally disclosed in U.S. Pat. No. 4,863,133. The mechanical arm 901 is sold by Leonard Medical, Inc. 1464 Holcomb Road, Huntington Valley, Pa., 19006. The mechanical arm 901 includes relatively movable parts, which permit movement and adjustment of the apparatus 100 in a variety in planes, directions, and orientations. The mechanical arm 901 permits easy movement when a vacuum is not applied to the arm 901. When a vacuum is applied to the arm 901, relative movement of the parts of the arm is resisted, and therefore adjustment of the apparatus 100 is difficult.

When the button 943 is depressed, the chamber 928 loses its vacuum and the pressure in the chamber increases toward ambient pressure. The passage 929 communicates this pressure increase to the mechanical arm 901, and thus the parts of the mechanical arm are free to move and allow for adjustment of the position of the apparatus 100 by the surgeon.

Accordingly, when the surgeon uses the apparatus 100, the support arm 900 is snapped into the socket of the mechanical arm 901 where it is held by the detent 906. The surgeon may then depress the button 943 and relatively move parts of the mechanical arm 901 as well as the apparatus 100 into the position where the surgeon desires the apparatus to be. This position may be where the central aperture 125 of the base 110 and the sleeve portion 600 are aligned with the proximal end 22 of the cannula 10 and the distal end 24 of the cannula 10 is located in an incision in the body of a patient. The camera head 99 (and the endoscope) may be mounted on the apparatus 100, and the surgeon may make adjustments prior to, and during, the surgical procedure as desired, as described above.

As viewed in FIG. 4, the fixed connection of the sleeve portion 600 to the support arm 900 may be made by the fasteners 599. The sleeve part 600 is axially offset from the gripper arms 511, 512 in order to allow the gripper arms to flex against the outer surface 28 of the cannula 10.

As viewed in FIG. 13, the sleeve part 600 may have an annular retaining lip 641 for engaging the proximal end 22 of the cannula 10. The retaining lip 641 extends radially inward toward the axis 14 and provides an upper limit stop that prevents the cannula 10 from extending upward (axially) from the central aperture 125. The upper edge of the retaining lip 641 is mounted flush with the upper surface area 121' of the first disk 121.

As viewed in FIGS. 13 and 14, the cannula 10 may be further axially secured within the sleeve part 600 by a cannula retainer structure 1000 (along with the retaining lip 641) located near the retaining lip at an inner surface 611 of the sleeve part 600. The retainer structure 1000 includes a first retention groove 1010 disposed on the inner surface 611 of the sleeve part 600, a corresponding second retention groove 1020 disposed in the outer surface 28 of the proximal end 22 of the cannula 10, and a split ring member 1030 for engaging both the first and second retention grooves. As viewed in FIG. 14, the split ring member 1030 (constructed of a metal such as steel) has a gap 1040. The ring member 1030, when located in retention groove 1010, may flex radially outward when the cannula 10 is axially inserted into the sleeve part 600 and into the ring member 1030. The outer surface 28 of the cannula 10 forces the ring member 1030 radially outward. The ring member 1030 then flexes back radially inward into the groove 1020 on the cannula 10 when the retention grooves 1010, 1020 are aligned. The ring member 1030 thereby axially secures the cannula 10 to the apparatus 100.

Figure 16:
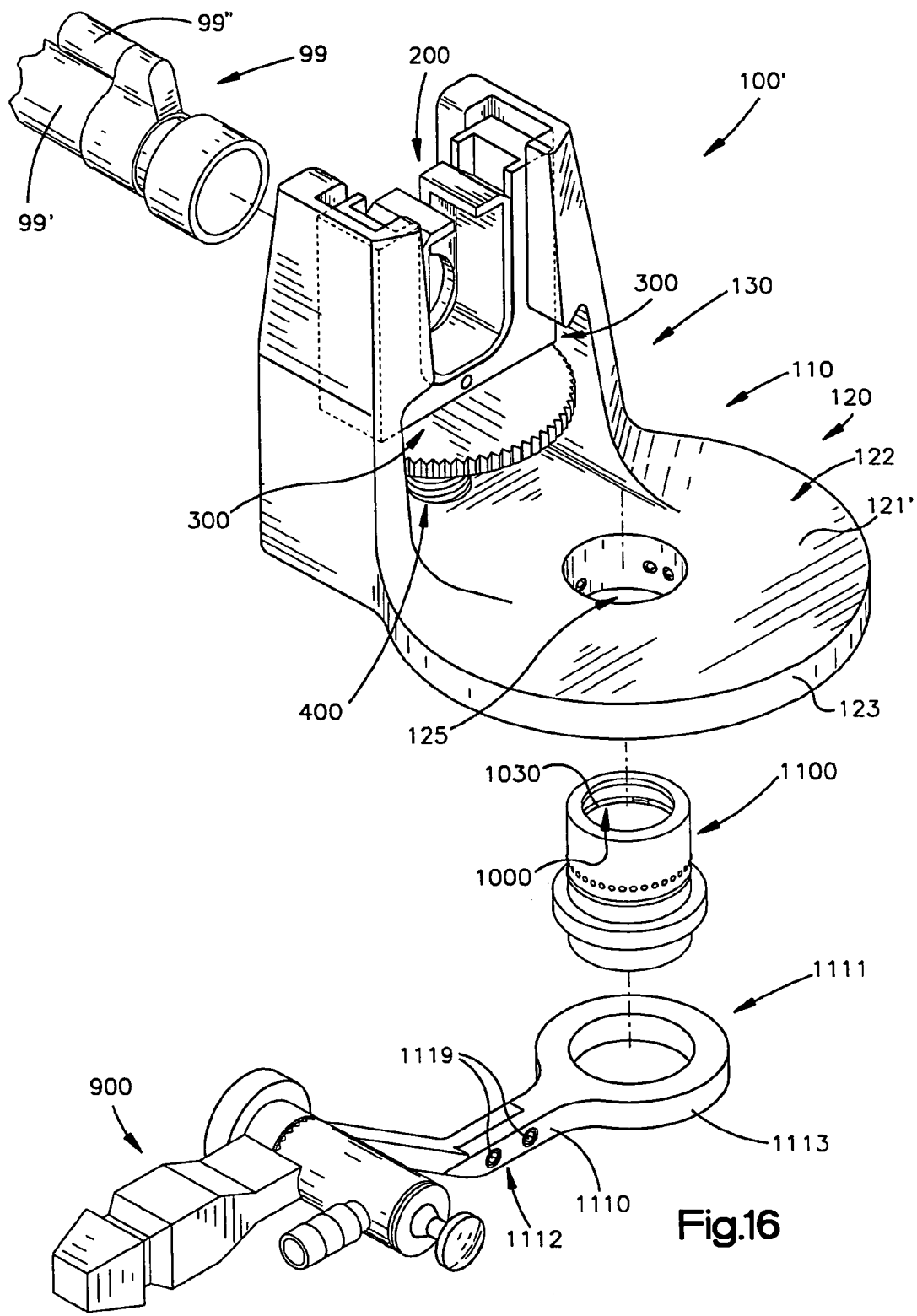
FIG. 16 is an exploded perspective view similar to FIG. 1 showing features of the present invention.

As viewed in FIGS. 15 and 16, the sleeve part 600, cannula clamp 500, and arm portion 902 may be replaced in an apparatus 100' by an alternative sleeve part 1100, a first arm portion 1110, and second arm portion 1120. The sleeve part 1100 is similar to the sleeve part 600 of FIGS. 1-14 except that it is not secured to the arm portion 902 by the fasteners 599. The sleeve part 1100 is a cylindrical tube symmetric about a central axis. The first arm portion 1110 has a first end 1111 with a sleeve retainer comprising a ring member 1113, that is press fit onto an outer surface 1101 of the lower end of the sleeve part 1100. The first arm portion 1110 may be constructed of an electrically insulating material such as plastic so that no electric charge is carried across the first arm portion. The sleeve 1100 is thus electrically insulated from the second arm portion 1120.

A second end 1112 of the first arm portion 1110 is secured to one end 1121 of the second arm portion 1120 by fasteners 1119, such as bolts or rivets. The opposite end 1122 of the second arm portion 1120 has the same configuration as that of the arm portion 902.

Figure 24:
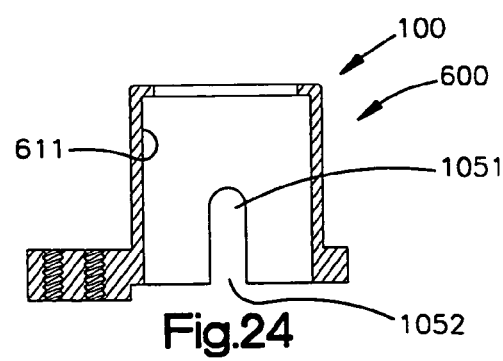
FIG. 24 is schematic detail view of another part that could be used in the apparatus of FIG. 16.

As viewed in FIG. 24, the sleeve part 600 of FIG. 13 may, instead of the split ring member 1030, alternatively have two diametrically opposed slots 1051 for increasing radial flexibility of the sleeve part 600. The outer surface 28 of the cannula 10 is slightly larger in diameter than the inner diameter of the inner surface 611 of the sleeve part 600. The cannula 10 is thereby frictionally secured within the sleeve part 600 by the clamping engagement of the sleeve part against the outer surface 28 of the cannula. The slots 1051 each have end portions 1052 that are open at the lower end of the sleeve part 600.

As viewed in FIG. 17, the inner surface 611 of the sleeve part 600 may further include an internal annular bead 1061 for engaging the outer surface 28 of the cannula 10. The internal diameter of the bead 1061 may be less than the outer diameter of the cannula 10. When the cannula 10 is inserted into the sleeve part 600, the internal diameter of the sleeve part 600 and the internal bead 1061 may increase to accommodate the cannula. After a retention groove of the cannula 10 reaches alignment with the internal bead 1061 of the sleeve part 600, the sleeve part can spring back toward its original diameter with the bead 1061 located in the retention groove on the cannula thereby axially securing the cannula within the sleeve part.

If the alternative internal bead feature 1061 is not used, a cannula with no groove may also be used. In this case the internal diameter of the sleeve 600 may be less than the outer diameter of the cannula 10. Thus, the sleeve part 600 would be expanded on insertion of the cannula 10 and would grip the outer surface 28 of the cannula.

Figure 18:
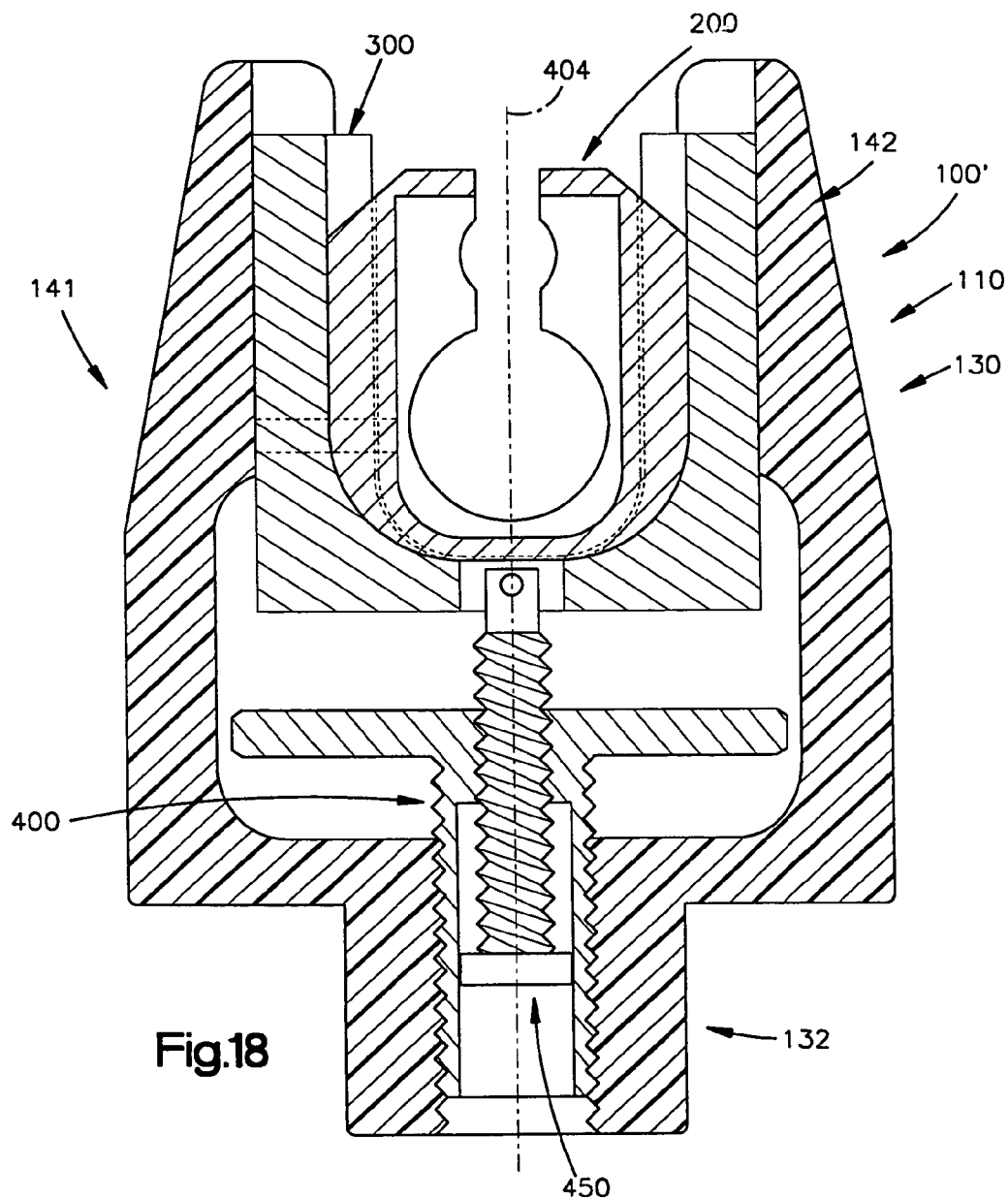
FIG. 18 is a schematic detail view of part of the apparatus of FIG. 13.

As viewed in FIGS. 15, 16, and 18, the apparatus 100' incorporates the alternative features of FIGS. 13 and 14 into the apparatus of FIGS. 1-12. The same numbering is applied to the apparatus 100' as that applied to the apparatus 100.

The entire apparatus 100 or 100' can be constructed from metal or any other suitable material having sufficient mechanical strength, flexibility, and durability. Certain parts may be made from materials permitting X-rays and other techniques for viewing the surgical site (i.e., radiopaque parts). Other parts may also be made from non-magnetic materials to reduce electromagnetic interference (i.e., electromagnetic insulating parts).

From the above description of the invention, those skilled in the art will perceive improvements, changes and modifications. Such improvements, changes and modifications within the skill of the art are intended to be covered by the appended claims.

Having described the invention, the following is claimed:

1. A method of viewing a surgical site in a patient through a passage in a device during surgery on the patient comprising:
   increasing an internal diameter of a sleeve as the device is inserted into the sleeve such that the sleeve clamps against the device;
   associating a base having a guide portion with the device;
   fixing a viewing device to a first part;
   engaging a second part to the guide portion; and
   moving the first and second parts together relative to the guide portion to change a position of the viewing device relative to the device and the patient.

2. The method as set forth in claim 1 including engaging a groove on an outer surface of the device with a split ring of a retainer to secure the device to the retainer and supporting the split ring with a sleeve.

3. The method as set forth in claim 2 including rotating the base relative to the sleeve about an axis of the device and indexing the base relative to the sleeve into one of a plurality of incremental relatively rotated positions relative to the sleeve.

4. The method as set forth in claim 1 including engaging an outer surface of the device with a sleeve and rotating the sleeve and the base relative to each other about an axis of the device.

5. The method as set forth in claim 4 including providing the sleeve with a radially inwardly extending annular retaining lip and engaging an upper end of the device with the retaining lip of the sleeve to limit axial movement of the device relative to the sleeve.

6. The method as set forth in claim 4 further including supporting the base and the sleeve with a sleeve retainer and press filling a member of the sleeve retainer onto an end portion of the sleeve.

7. The method as set forth in claim 1 including engaging the device with a sleeve, securing the sleeve to a support structure with a support arm, engaging the sleeve with a first portion of the support arm and providing the support arm with an electrically insulating material electrically insulating the sleeve from a second portion of the support arm that interconnects the first portion and the support structure.

8. The method as set forth in claim 1 including slidably engaging at least one rail member of the first part with a guide track of the second part.

9. The method as set forth in claim 1 including rotating a second threaded spindle about an axis relative to a first threaded spindle to move the first and second parts together relative to the guide portion and limiting axial displacement of the first threaded spindle relative to the second threaded spindle.

10. The method as set forth in claim 9 including engaging a radially extending shoulder portion of the second threaded spindle with a lip portion of the first threaded spindle.

11. The method as set forth in claim 1 including expanding the device.

12. The method as set forth in claim 11 including inserting an expansion tool into the passage in the device and actuating the expansion tool to expand the device.

13. A method of viewing a surgical site in a patient through a passage in a device during surgery on the patient comprising:
engaging a groove on the outer surface of the device with a split ring of a retainer to secure the device to the retainer;
receiving the device in a sleeve of the retainer;
supporting the split ring in the sleeve of the retainer; and
rotating a base relative to the sleeve about an axis of the device.

14. The method as set forth in claim 13 including fixing a first part to a viewing device, engaging a second part to a guide portion of the base, and moving the first and second parts together relative to the guide portion.

15. The method as set forth in claim 13 including supporting the base and the sleeve with a sleeve retainer and providing the sleeve retainer with a ring member press fit onto an end portion of the sleeve.

16. The method as set forth in claim 13 including increasing an internal diameter of the sleeve as the device is inserted into the sleeve such that the sleeve clamps against the device.

17. The method as set forth in claim 13 including engaging an annular retaining lip of the sleeve with an upper end of the device and limiting axial movement of the device relative to the sleeve.

18. The method as set forth in claim 13 including securing the device to the sleeve with an annular bead disposed on an inner surface of the sleeve.

19. The method as set forth in claim 13 including expanding the device.

20. The method as set forth in claim 19 including inserting an expansion tool into the passage in the device and actuating the expansion tool to expand the device.

21. A method for viewing a surgical site in a patient through a passage in a device during surgery on the patient comprising:
supporting a viewing element with a base; receiving the device in a sleeve;
increasing an internal diameter of the sleeve as the device is inserted into the sleeve such that the sleeve clamps against the device;
rotating the base and the sleeve relative to each other about an axis of the device;
supporting the sleeve and the base with a sleeve retainer; and
press filling a member of the sleeve retainer onto an end portion of the sleeve.

22. The method as set forth in claim 21 including fixing a first part to the viewing element, slidably engaging a second part to the base, and vertically moving the first part and the second part together relative to the base.

23. The method as set forth in claim 21 including engaging a first groove on the outer surface of the device and a second groove on an inner surface of the sleeve with a split ring.

24. The method as set forth in claim 21 including rotating the base relative to the sleeve about an axis of the device and retaining the base at one of a plurality of incremental relatively rotated positions relative to the sleeve.

25. The method as set forth in claim 21 including electrically insulating the sleeve.

26. The method as set forth in claim 21 including rotating a second threaded spindle about an axis relative to a first threaded spindle to axially adjust the viewing element relative to the base and limiting axial displacement of the first threaded spindle relative to the second threaded spindle.

27. The method as set forth in claim 26 including engaging a lip portion of the first threaded spindle with a radially extending shoulder portion of the second threaded spindle.

28. The method as set forth in claim 21 including expanding the device.

29. The method as set forth in claim 28 including inserting an expansion tool into the passage in the device and actuating the expansion tool to expand the device.

30. A method for viewing a surgical site in a patient through a passage in a device during surgery on the patient comprising:
supporting a viewing element with a base; receiving the device in a sleeve;
rotating the base and the sleeve relative to each other about an axis of the device;
securing the sleeve to a support structure with a support arm; and
providing the support arm with a first portion for connection to the sleeve and a second portion for interconnecting the first portion and the support structure, the first portion including an electrically insulating material electrically insulating the sleeve from the second portion.

31. The method as set forth in claim 30 including fixing a first part to the viewing element, adjustably engaging a second part to the base, and vertically moving the first part and the second part together relative to the base.

32. The method as set forth in claim 31 including providing the sleeve with a radially inwardly extending annular retaining lip and engaging an upper end of the device with the retaining lip of the sleeve to limit axial movement of the device relative to the sleeve.

33. The method as set forth in claim 30 including engaging a first groove on the outer surface of the device and a second groove on an inner surface of the sleeve with a split ring.

34. The method as set forth in claim 33 including retaining the base at one of a plurality of incremental relatively rotated positions relative to the sleeve.

35. The method as set forth in claim 30 including increasing an internal diameter of an annular bead on the sleeve as the device is inserted into the sleeve, such that the sleeve clamps against the device.

36. The method as set forth in claim 30 including expanding the device.

37. The method as set forth in claim 36 including inserting an expansion tool into the passage in the device and actuating the expansion tool to expand the device.

38. A method for viewing a surgical site in a patient during surgery on the patient comprising:
fixing a first part to a viewing device;
moving the first part and a second part connected with the first part together relative to a guide portion of a base;
moving the first and second parts relative to the guide portion with a screw mechanism connected to the second part; and
securing the second part to the screw mechanism with a pin, the pin being press fit into recesses in both the second part and the screw mechanism.

39. The method as set forth in claim 38 including receiving a device defining a passage in a sleeve and engaging a groove on an outer surface of the device with a split ring to secure the device to the sleeve.

40. The method as set forth in-claim 39 including engaging an upper end of the device and limiting axial movement of the device relative to the sleeve with an annular retaining lip on the sleeve.

41. The method as set forth in claim 39 including rotating the base relative to the sleeve about an axis of the sleeve and retaining the base at one of a plurality of incremental relatively rotated positions relative to the sleeve.

42. The method as set forth in claim 38 including engaging an outer surface of a device defining a passage with a sleeve and rotating the sleeve and the base relative to each other about an axis of the device.

43. The method as set forth in claim 42 including supporting the sleeve and the base with a sleeve retainer having a ring member press fit onto an end portion of the sleeve.

44. The method as set forth in claim 38 including engaging an outer surface of a device defining a passage with a cylindrical sleeve having an internal bead and increasing an internal diameter of the sleeve as the device is inserted into the sleeve so that the sleeve clamps the device.

45. The method as set forth in claim 38 including receiving a device defining a passage in the base and expanding the device.

46. The method as set forth in claim 45 including inserting an expansion tool into the passage in the device and actuating the expansion tool to expand the device.

47. A method for viewing a surgical site in a patient through a passage in a device during surgery on the patient comprising:
supporting a viewing element;
engaging an outer surface of the device with a sleeve;
rotating a base and the sleeve relative to each other about an axis of the device;
increasing an internal diameter of the sleeve as the device is inserted into the sleeve so that the sleeve grips the device; and
expanding the device.

48. The method as set forth in claim 47 including engaging a groove on the outer surface of the device with a split ring.

49. The method as set forth in claim 48 including rotating the base relative to the sleeve about an axis of the device and retaining the base in one of a plurality of incremental relatively rotated positions relative to the sleeve.

50. The method as set forth in claim 47 including supporting the base and the sleeve with a sleeve retainer having a ring member press fit onto an end portion of the sleeve.

51. The method as set forth in claim 47 including securing the sleeve to a support structure with a support arm having a first portion for connection to the sleeve and a second portion for interconnecting the first portion and the support structure, the first portion including an electrically insulating material electrically insulating the sleeve from the second portion.

52. The method as set forth in claim 47 including inserting an expansion tool into the passage in the device and actuating the expansion tool to expand the device.

53. A method for viewing a surgical site in a patient through a passage in a device during surgery on the patient including:
fixing a structure to a viewing device;
engaging a guide portion of a base with the structure;
moving the structure relative to the guide portion;
rotating a portion of a screw mechanism connected between the base and the structure to slide the structure relative to the guide portion to change a position of the viewing device relative to the patient; and
providing the screw mechanism with a first threaded spindle having female threads and a second threaded spindle rotatable about an axis relative to the female threads in the first threaded spindle, the first threaded spindle having a lip portion for limiting axial displacement of the first threaded spindle relative to the second threaded spindle.

54. The method as set forth in claim 53 including fixing a first part of the structure to the viewing device and moving the first part and a second part of the structure together relative to the guide portion.

55. The method as set forth in claim 53 including engaging an outer surface of the device with a sleeve and engaging a groove on the outer surface of the device with a split ring supported by the sleeve.

56. The method as set forth in claim 55 including rotating the base relative to the sleeve about an axis of the device and retaining the base in one of a plurality of incremental relatively rotated positions relative to the device.

57. The method as set forth in claim 55 including supporting the base and the sleeve with a sleeve retainer having a ring member press fit onto an end portion of the sleeve.

58. The method as set fort in claim 53 including expanding the device.

59. The method as set forth in claim 58 including inserting an expansion tool into the passage in the device and actuating the expansion tool to expand the device.

* * * * *